(12) United States Patent
Tarnopolsky et al.

(10) Patent No.: US 10,064,919 B2
(45) Date of Patent: Sep. 4, 2018

(54) THERAPEUTIC METHOD OF INDUCING MITOCHONDRIAL BIOGENESIS TO TREAT SKIN AND MUSCLE PATHOLOGIES

(71) Applicant: EXERKINE CORPORATION, Hamilton (CA)

(72) Inventors: Mark Tarnopolsky, Hamilton (CA); Justin Crane, Boston, MA (US)

(73) Assignee: EXERKINE CORPORATION, Hamilton, Ontario (CA)

( * ) Notice: Subject to any disclaimer, the term of this patent is extended or adjusted under 35 U.S.C. 154(b) by 0 days.

(21) Appl. No.: 14/992,969

(22) Filed: Jan. 11, 2016

(65) Prior Publication Data

US 2016/0354442 A1 Dec. 8, 2016

Related U.S. Application Data

(63) Continuation-in-part of application No. PCT/CA2014/000568, filed on Jul. 11, 2014.

(60) Provisional application No. 61/845,159, filed on Jul. 11, 2013.

(51) Int. Cl.

| | |
|---|---|
| *A61K 38/20* | (2006.01) |
| *C07K 14/54* | (2006.01) |
| *A61K 38/18* | (2006.01) |
| *A61K 31/10* | (2006.01) |
| *A61K 31/355* | (2006.01) |
| *A61K 31/375* | (2006.01) |
| *A61K 31/40* | (2006.01) |
| *A61K 31/713* | (2006.01) |
| *A61K 8/60* | (2006.01) |
| *A61K 8/64* | (2006.01) |
| *A61K 9/00* | (2006.01) |
| *A61K 31/7088* | (2006.01) |
| *A61K 38/22* | (2006.01) |
| *A61K 45/06* | (2006.01) |
| *A61Q 19/08* | (2006.01) |

(52) U.S. Cl.
CPC .......... *A61K 38/2086* (2013.01); *A61K 8/606* (2013.01); *A61K 8/64* (2013.01); *A61K 9/0014* (2013.01); *A61K 9/0019* (2013.01); *A61K 31/10* (2013.01); *A61K 31/355* (2013.01); *A61K 31/375* (2013.01); *A61K 31/40* (2013.01); *A61K 31/7088* (2013.01); *A61K 31/713* (2013.01); *A61K 38/18* (2013.01); *A61K 38/22* (2013.01); *A61K 45/06* (2013.01); *A61Q 19/08* (2013.01); *C07K 14/5443* (2013.01)

(58) Field of Classification Search
None
See application file for complete search history.

(56) References Cited

U.S. PATENT DOCUMENTS

2006/0257361 A1* 11/2006 Watanabe .......... C07K 14/5443
424/85.2
2007/0110714 A1* 5/2007 Hayashi ............. A61K 31/7004
424/85.2

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Pistilli et al, The Journal of Clinical Investigation, Aug. 2011, vol. 121, No. 8, pp. 3120-3122.*
Quin et al, Endocrinology, Jan. 2013, 154(1):232-245, Published Online Nov. 16, 2012.*
Van der Windt, Immunity, 2012, vol. 36, pp. 68-78.*
Crystal R, Science, 1995. vol. 270, pp. 404-410.*
Juengst et al, British Medical Journal; 2003, vol. 326, pp. 1410-1411.*
Rubanyi , Mol Aspects Med , 2001 vol. 22, pp. 113-142.*
Perez et al, Blood, 2005, vol. 106, No. 1, pp. 158-166.*
Moustaki et al, Cancer Immunology Immunotherapy, 2011; vol. 620, pp. 1683-1695.*
Adrenal Cortical Steroids, Drug Facts and Comparison, 1997.*

* cited by examiner

*Primary Examiner* — Bridget E Bunner
*Assistant Examiner* — Fozia Hamud
(74) *Attorney, Agent, or Firm* — Milstein Zhang & Wu LLC

(57) ABSTRACT

A method of inducing mitochondrial biogenesis in a mammal is provided. The method comprises the step of administering to the mammal an interleukin-15 or nucleic acid encoding an interleukin-15 to the mammal.

13 Claims, 20 Drawing Sheets
Specification includes a Sequence Listing.

Figure 1 – continued
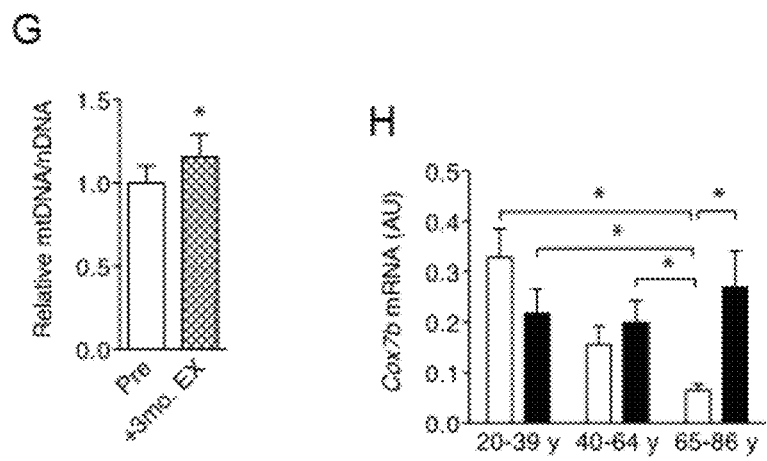

Figure 3 - continued
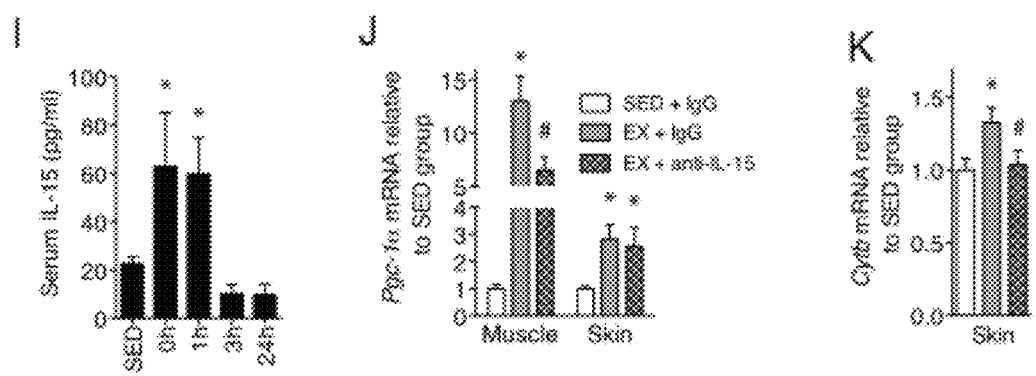

Figure 4 - continued
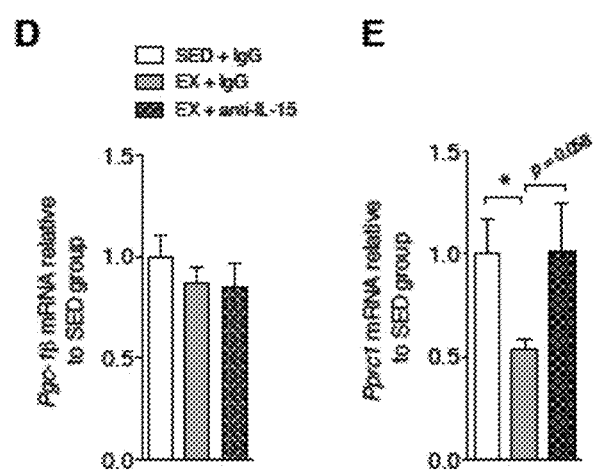

Figure 5 – continued
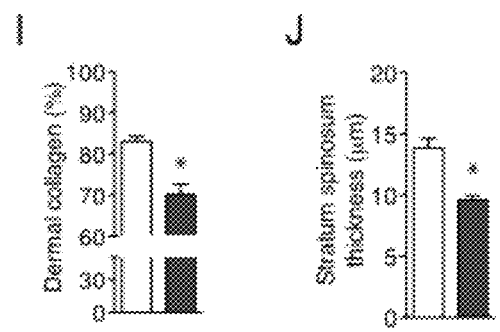

Figure 6 - continued
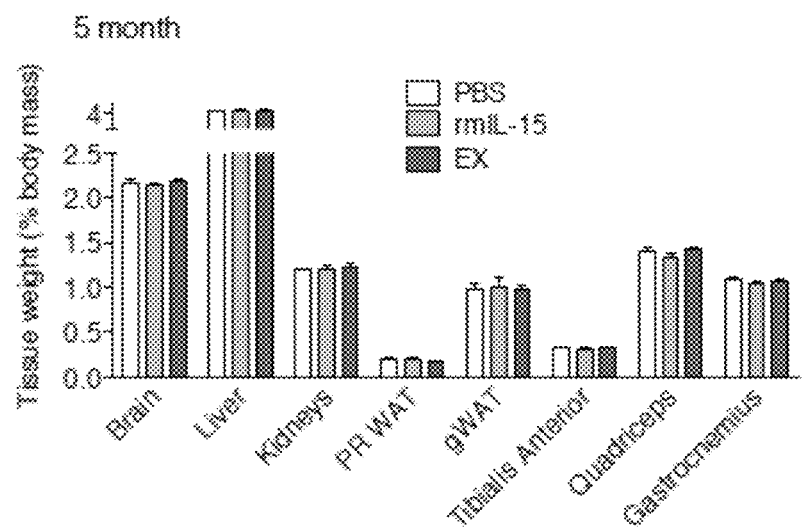
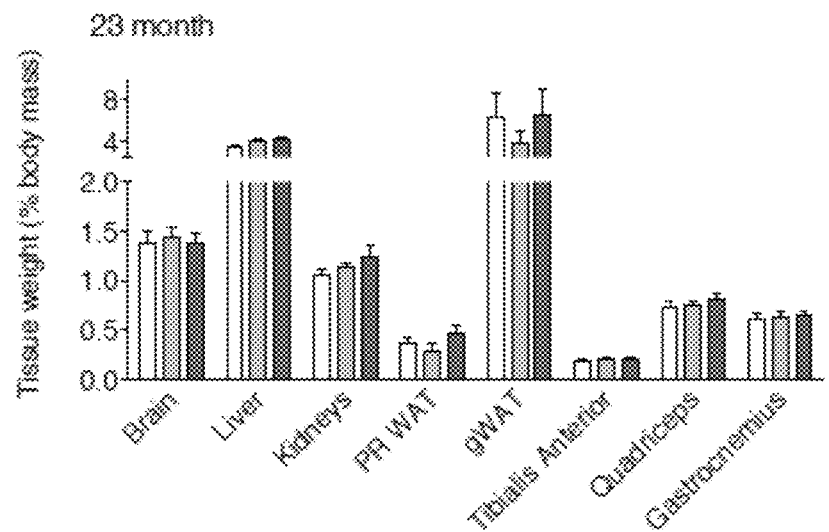

Figure 6 - continued
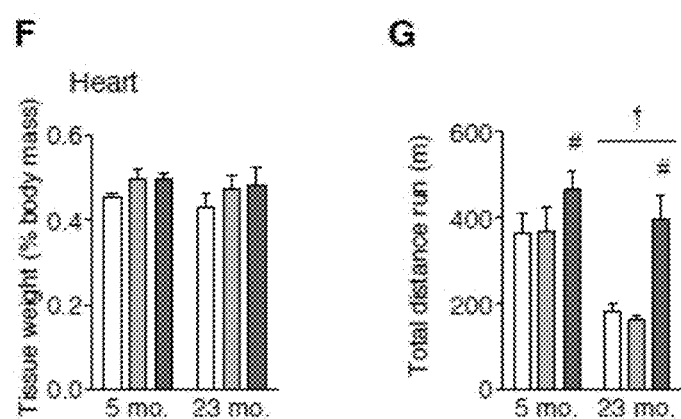

Figure 7 - continued
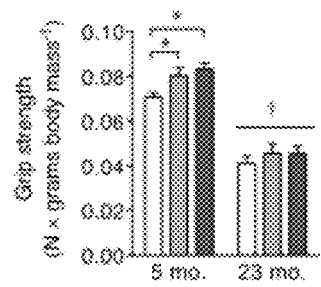
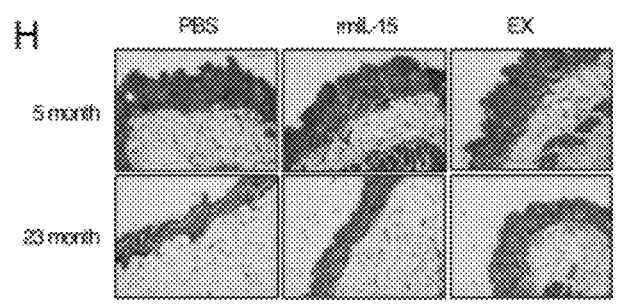
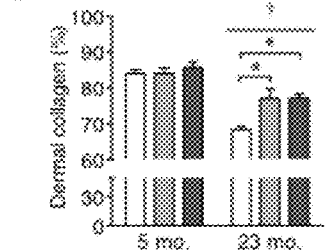
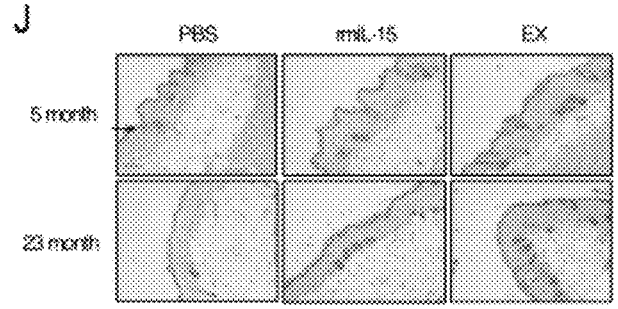
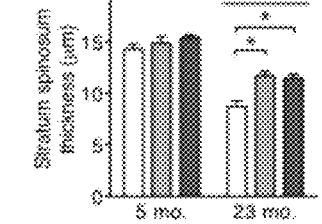

MRISKPHLRS ISIQCYLCLL LNSHFLTEAG IHVFILGCFS AGLPKTEANW
VNVISDLKKI EDLIQSMHID ATLYTESDVH PSCKVTAMKC FLLELQVISL
ESGDASIHDT VENLIILANNSLSSNGNVTE SGCKECEELE EKNIKEFLQS
FVHIVQMFIN TS (SEQ ID NO: 1)

B)

MKILKPYMRN TSISCYLCFL LNSHFLTEAG IHVFILGCVS VGLPKTEANW
IDVRYDLEKESLIQSIHID TTLYTDSDFH PSCKVTAMNC FLLELQVILH
EYSNMTLNET VRNVLYLANSTLSSNKNVAE SGCKECEELE EKTFTEFLQS
FIRIVQMFIN TS (SEQ ID NO: 2)

C)

MKILKPYMRN TSILYYLCFL LNSHFLTEAG IHVFILGCVS VGLPKTEANW
IDVRYDLEKI ESLIQFIHID TTLYTDSDFH PSCKVTAMNC FLLELQVILH
EYSNMTLNET VRNVLYLANSTLSSNKNVIE SGCKECEELE ERNFTEFLQS
FIHIVQMFIN TS (SEQ ID NO: 3)

D)

MRISKPHLRS TSIQCYLCLL LNSHFLTEAG IHVFILGCIS AGLPKTEANW
QDVILDLEKI DNLIQSIHMD TTLYTESDVH PSCKVTAMKC FLLELGVISL
ESGSHPIKEA VENLIILANS DLSSKGNITE TGCKECEELE EKSIKEFLQS
FVHIVQMFIN SS (SEQ ID NO: 4)

```
gttgggactc cgggtggcag gcgcccgggg gaatcccagc tgactcgctc actgccttcg 61
aagtccggcg cccccgggga gggaactggg tggccgcacc ctcccggctg cggtggctgt 121
cgccccccac cctgcagcca ggactcgatg gagaatccat tccaatatat ggccatgtgg 181
ctctttggag caatgttcca tcatgttcca tgctgctgac gtcacatgga gcacagaaat 241
caatgttagc agatagccag cccatacaag atcgtattgt attgtaggag gcattgtgga 301
tggatggctg ctggaaaccc cttgccatag ccagctcttc ttcaatactt aaggatttac 361
cgtggctttg agtaatgaga atttcgaaac cacatttgag aagtatttcc atccagtgct 421
acttgtgttt acttctaaac agtcattttc taactgaagc tggcattcat gtcttcattt 481
tgggctgttt cagtgcaggg cttcctaaaa cagaagccaa ctgggtgaat gtaataagtg 541
atttgaaaaa aattgaagat cttattcaat ctatgcatat tgatgctact ttatatacgg 601
aaagtgatgt tcaccccagt tgcaaagtaa cagcaatgaa gtgcttttctc ttggagttac 661
aagttatttc acttgagtcc ggagatgcaa gtattcatga tacagtagaa aatctgatca 721
tcctagcaaa caacagtttg tcttctaatg ggaatgtaac agaatctgga tgcaaagaat 781
gtgaggaact ggaggaaaaa aatattaaag aattttttgca gagttttgta catattgtcc 841
aaatgttcat caacacttct tgattgcaat tgattctttt taaagtgttt ctgttattaa 901
caaacatcac tctgctgctt agacataaca aaacactcgg catttcaaat gtgctgtcaa 961
aacaagtttt tctgtcaaga agatgatcag accttggatc agatgaactc ttagaaatga 1021
aggcagaaaa atgtcattga gtaatatagt gactatgaac ttctctcaga cttacttttac 1081
tcattttttt aattattat tgaaattgta catatttgtg gaataatgta aaatgttgaa 1141
taaaaatatg tacaagtgtt gttttttaag ttgcactgat atttttacctc ttattgcaaa 1201
atagcatttg tttaagggtg atagtcaaat tatgtattgg tgggctggg taccaatgct 1261
gcaggtcaac agctatgctg gtaggctcct gccagtgtgg aaccactgac tactggctct 1321
cattgacttc cttactaagc atagcaaaca gaggaagaat ttgttatcag taagaaaaag 1381
aagaactata tgtgaatcct cttctttata ctgtaattta gttattgatg tataaagcaa 1441
ctgttatgaa ataaagaaat tgcaataact ggcatataat gtccatcagt aaatcttggt 1501
ggtggtggca ataataaact tctactgata ggtagaatgg tgtgcaagct tgtccaatca 1561
cggattgcag gccacatgcg gccaggaca acttttgaatg tggcccaaca caaattcata 1621
aacttttcata catctctgtt ttagctcatc agctatcatt agcggtagtg tatttaaagt 1681
gtggccaag acaattcttc ttattccaat gtggcccagg gaaatcaaaa gattggatgc 1741
ccctggtata gaaaactaat agtgacagtg ttcatatttc atgctttccc aaatacaggt 1801
atttttatttt cacattcttt ttgccatgtt tatataataa taaagaaaaa ccctgttgat 1861
ttgttggagc cattgttatc tgacagaaaa taattgttta tattttttgc actacactgt 1921
ctaaaattag caagctctct tctaatggaa ctgtaagaaa gatgaaatat ttttgttttta 1981
ttataaattt atttcaccttt aaaaaaaaaa aa
```

(SEQ ID NO: 5)

```
   1 ttcttgacca agacttcaat actcagtggc actgtattcc ccttctgtcc agccactctt
  61 cccagagtt ctcttcttca tcctcccct tgcagagtag ggcagcttga aggtcctcct
 121 gcaagtctct cccaattctc tgcgcccaaa agacttgcag tgcatctcct tacgcgctgc
 181 aggpaccttg ccagggcagg actgccccg cccagttgca gagttggacg aagacgggat
 241 cctgctgtgt ttggaaggct gagttccaca tctaacagct cagagagaat ccaccttgac
 301 acatggcct ctggctcttc aaagcactgc ctcttcatgg tccttgctgg tgaggtcctt
 361 aagaacacag aaacccatgt cagcagataa ccagcctaca ggaggccaag aagagttctg
 421 gatggatggc agctggaagc ccatcgccat agccagctca tcttcaacat tgaagctctt
 481 acctgggcat taagtaatga aaattttgaa accatatatg aggaatacat ccatctcgtg
 541 ctacttgtgt ttccttctaa acagtcactt tttaactgag gctggcattc atgtcttcat
 601 tttggctgt gtcagtgtag gtctccctaa aacagaggcc aactggatag atgtaagata
 661 tgacctggag aaaattgaaa gccttattca atctattcat attgacacca ctttatacac
 721 tgacagtgac tttcatccca gttgcaaagt tactgcaatg aactgctttc tcctggaatt
 781 gcaggttatt ttacatgagt acagtaacat gactcttaat gaaacagtaa gaaacgtgct
 841 ctaccttgca aacagcactc tgtcttctaa caagaatgta gcagaatctg gctgcaagga
 901 atgtgaggag ctggaggaga aaaccttcac agagttttg caaagcttta tacgcattgt
 961 ccaaatgttc atcaacaagt cctgactgca tgcgagcctc ttccgtgttt ctgttattaa
1021 ggtacctcca cctgctgctc agaggcagca cagtccatg catttgaaat ctgctgggca
1081 aactaagctt cctaacaagg agataatgag ccacttggat cacatgaaat cttggaaatg
1141 aagagaggaa aagagctcgt ctcagactta ttttgcttg cttattttta attrattgct
1201 tcattgtac atatttgtaa tataacagaa gatgtggaat aaagttgtat ggatatttta
1261 tcaattgaaa tttaaaaaaa aaaaaa
```

(SEQ ID NO: 6)

A

B

SEQUENCE LISTING

```
<160> NUMBER OF SEQ ID NOS: 6

<210> SEQ ID NO 1
<211> LENGTH: 162
<212> TYPE: PRT
<213> ORGANISM: Homo sapiens

<400> SEQUENCE: 1

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser
```

<210> SEQ ID NO 2
<211> LENGTH: 161
<212> TYPE: PRT
<213> ORGANISM: Mus sp.

<400> SEQUENCE: 2

```
Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Glu Ser Leu Ile Gln
    50                  55                  60

Ser Ile His Ile Asp Thr Thr Leu Tyr Thr Asp Ser Asp Phe His Pro
65                  70                  75                  80

Ser Cys Lys Val Thr Ala Met Asn Cys Phe Leu Leu Glu Leu Gln Val
                85                  90                  95

Ile Leu His Glu Tyr Ser Asn Met Thr Leu Asn Glu Thr Val Arg Asn
            100                 105                 110

Val Leu Tyr Leu Ala Asn Ser Thr Leu Ser Ser Asn Lys Asn Val Ala
        115                 120                 125

Glu Ser Gly Cys Lys Glu Cys Glu Glu Leu Glu Glu Lys Thr Phe Thr
    130                 135                 140

Glu Phe Leu Gln Ser Phe Ile Arg Ile Val Gln Met Phe Ile Asn Thr
145                 150                 155                 160

Ser
```

<210> SEQ ID NO 3
<211> LENGTH: 162
<212> TYPE: PRT
<213> ORGANISM: Rattus sp.

<400> SEQUENCE: 3

```
Met Lys Ile Leu Lys Pro Tyr Met Arg Asn Thr Ser Ile Leu Tyr Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Phe Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ile Glu Ser Gly Cys Lys Glu Cys Glu Glu Leu Glu Glu Arg Asn Phe
    130                 135                 140

Thr Glu Phe Leu Gln Ser Phe Ile His Ile Val Gln Met Phe Ile Asn
145                 150                 155                 160
```

Thr Ser

<210> SEQ ID NO 4
<211> LENGTH: 162
<212> TYPE: PRT
<213> ORGANISM: Canis sp.

<400> SEQUENCE: 4

Met Arg Ile Ser Lys Pro His Leu Arg Ser Thr Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Ile Ser Ala Gly Leu Pro Lys Thr Glu Ala
        35                  40                  45

Asn Trp Gln Asp Val Ile Leu Asp Leu Glu Lys Ile Asp Asn Leu Ile
    50                  55                  60

Gln Ser Ile His Met Asp Thr Thr Leu Tyr Thr Glu Ser Asp Val His
65                  70                  75                  80

Pro Ser Cys Lys Val Thr Ala Met Lys Cys Phe Leu Leu Glu Leu Gly
                85                  90                  95

Val Ile Ser Leu Glu Ser Gly Ser His Pro Ile Lys Glu Ala Val Glu
            100                 105                 110

Asn Leu Ile Ile Leu Ala Asn Ser Asp Leu Ser Ser Lys Gly Asn Ile
        115                 120                 125

Thr Glu Thr Gly Cys Lys Glu Cys Glu Glu Leu Glu Glu Lys Ser Ile
130                 135                 140

Lys Glu Phe Leu Gln Ser Phe Val His Ile Val Gln Met Phe Ile Asn
145                 150                 155                 160

Ser Ser

<210> SEQ ID NO 5
<211> LENGTH: 2012
<212> TYPE: DNA
<213> ORGANISM: Homo sapiens

<400> SEQUENCE: 5
gttgggactc cgggtggcag gcgcccgggg gaatcccagc tgactcgctc actgccttcg      60
aagtccggcg cccccgggga gggaactggg tggccgcacc ctcccggctg cggtggctgt     120 cgcccccac cctgcagcca ggactcgatg gagaatccat tccaatatat ggccatgtgg      180
ctctttggag caatgttcca tcatgttcca tgctgctgac gtcacatgga gcacagaaat     240
caatgttagc agatagccag cccatacaag atcgtattgt attgtaggag gcattgtgga     300
tggatggctg ctggaaaccc cttgccatag ccagctcttc ttcaatactt aaggatttac     360
cgtggctttg agtaatgaga atttcgaaac cacatttgag aagtatttcc atccagtgct     420
acttgtgttt acttctaaac agtcattttc taactgaagc tggcattcat gtcttcattt     480
tgggctgttt cagtgcaggg cttcctaaaa cagaagccaa ctgggtgaat gtaataagtg     540
atttgaaaaa aattgaagat cttattcaat ctatgcatat tgatgctact ttatatacgg     600
aaagtgatgt tcaccccagt tgcaaagtaa cagcaatgaa gtgctttctc ttggagttac     660
aagttatttc acttgagtcc ggagatgcaa gtattcatga tacagtagaa aatctgatca     720
tcctagcaaa caacagtttg tcttctaatg ggaatgtaac agaatctgga tgcaaagaat     780
gtgaggaact ggaggaaaaa aatattaaag aattttgca gagttttgta catattgtcc      840
aaatgttcat caacacttct tgattgcaat tgattctttt taaagtgttt ctgttattaa     900

```
caaacatcac tctgctgctt agacataaca aaacactcgg catttcaaat gtgctgtcaa      960
aacaagtttt tctgtcaaga agatgatcag accttggatc agatgaactc ttagaaatga     1020
aggcagaaaa atgtcattga gtaatatagt gactatgaac ttctctcaga cttactttac     1080 tcatttttt aatttattat tgaaattgta catatttgtg gaataatgta aaatgttgaa      1140
taaaaatatg tacaagtgtt gttttttaag ttgcactgat attttacctc ttattgcaaa     1200
atagcatttg tttaagggtg atagtcaaat tatgtattgg tggggctggg taccaatgct     1260
gcaggtcaac agctatgctg gtaggctcct gccagtgtgg aaccactgac tactggctct     1320
cattgacttc cttactaagc atagcaaaca gaggaagaat ttgttatcag taagaaaaag     1380
aagaactata tgtgaatcct cttctttata ctgtaattta gttattgatg tataaagcaa     1440
ctgttatgaa ataagaaat tgcaataact ggcatataat gtccatcagt aaatcttggt      1500
ggtggtggca ataataaact tctactgata ggtagaatgg tgtgcaagct tgtccaatca     1560
cggattgcag gccacatgcg gcccaggaca actttgaatg tggcccaaca caaattcata     1620
aactttcata catctcgttt ttagctcatc agctatcatt agcggtagtg tatttaaagt     1680
gtggcccaag acaattcttc ttattccaat gtggcccagg aaatcaaaa gattggatgc      1740 ccctggtata gaaaactaat agtgacagtg ttcatatttc atgcttccc aaatacaggt      1800 attttatttt cacattcttt ttgccatgtt tatataataa aaagaaaaa ccctgttgat      1860 ttgttggagc cattgttatc tgacagaaaa taattgttta tattttttgc actacactgt     1920
ctaaaattag caagctctct tctaatgaaa ctgtaagaaa gatgaaatat ttttgtttta     1980
ttataaattt atttcacctt aaaaaaaaaa aa                                    2012

<210> SEQ ID NO 6
<211> LENGTH: 1287
<212> TYPE: DNA
<213> ORGANISM: Mus sp.

<400> SEQUENCE: 6
ttcttgacca agacttcaat actcagtggc actgtattcc ccttctgtcc agccactctt       60
ccccagagtt ctcttcttca tcctcccct tgcagagtag ggcagcttgc aggtcctcct      120
gcaagtctct cccaattctc tgcgcccaaa agacttgcag tgcatctcct tacgcgctgc     180
agggaccttg ccagggcagg actgccccg cccagttgca gagttggacg aagacgggat      240
cctgctgtgt ttggaaggct gagttccaca tctaacagct cagagagaat ccaccttgac     300
acatggcccc ctggctcttc aaagcactgc ctcttcatgg tccttgctgg tgaggtcctt     360
aagaacacag aaacccatgt cagcagataa ccagcctaca ggaggccaag aagagttctg     420
gatggatggc agctggaagc ccatcgccat agccagctca tcttcaacat tgaagctctt     480
acctgggcat taagtaatga aaattttgaa accatatatg aggaatacat ccatctcgtg     540
ctacttgtgt ttccttctaa acagtcactt tttaactgag gctggcattc atgtcttcat     600
tttgggctgt gtcagtgtag gtctccctaa aacagaggcc aactggatag atgtaagata     660
tgacctggag aaaattgaaa gccttattca atctattcat attgacacca ctttatacac     720
tgacagtgac tttcatccca gttgcaaagt tactgcaatg aactgctttc tcctggaatt     780
gcaggttatt ttacatgagt acagtaacat gactcttaat gaaacagtaa gaaacgtgct     840
ctaccttgca aacagcactc tgtcttctaa caagaatgta gcagaatctg gctgcaagga     900
atgtgaggag ctggaggaga aaaccttcac agagtttttg caaagcttta tacgcattgt     960
```

-continued

```
ccaaatgttc atcaacacgt cctgactgca tgcgagcctc ttccgtgttt ctgttattaa    1020
ggtacctcca cctgctgctc agaggcagca cagctccatg catttgaaat ctgctgggca    1080
aactaagctt cctaacaagg agataatgag ccacttggat cacatgaaat cttggaaatg    1140
aagagaggaa aagagctcgt ctcagactta tttttgcttg cttatttta  atttattgct    1200 tcatttgtac atatttgtaa tataacagaa gatgtggaat aaagttgtat ggatatttta    1260
tcaattgaaa tttaaaaaaa aaaaaaa                                        1287
```

THERAPEUTIC METHOD OF INDUCING MITOCHONDRIAL BIOGENESIS TO TREAT SKIN AND MUSCLE PATHOLOGIES

PRIORITY CLAIMS AND RELATED PATENT APPLICATIONS

This application claims the benefit of priority, under 35 U.S.C. § 120, from the US designation of International Application No. PCT/CA2014/000568, filed on Jul. 11, 2014, which claims benefit of priority from U.S. Provisional Application Ser. No. 61/845,159, filed on Jul. 11, 2013, the entire content of each of which is incorporated herein by reference in its entirety for all purposes.

FIELD OF THE INVENTION

The present invention relates to a method of inducing mitochondrial biogenesis to treat skin and muscle pathologies, and more particularly, to a method of treating skin and muscle pathologies resulting from mitochondrial dysfunction.

BACKGROUND OF THE INVENTION

Skin is the largest organ in the human body and the primary physical barrier against infection and disease. Aging is associated with the deterioration of the dermal and epidermal layers of the skin, resulting from reductions in cell proliferation, collagen synthesis, extracellular matrix remodelling and altered epidermal morphology. Additionally, recent research indicates that aged and senescent dermal fibroblasts exhibit reduced energy metabolism, higher mitochondrial oxidative stress, and mitochondrial DNA (mtDNA) deletions, reflecting characteristics of the mitochondrial free radical theory of aging. In agreement, the deletion of a free radical scavenger within the mitochondria, superoxide dismutase 2, from connective tissue results in premature skin aging and depleting mtDNA in dermal fibroblasts mimics the gene profile of photoaging. Conversely, treatment with PPAR agonists that stimulate mitochondrial metabolism and cell proliferation improves skin wound healing and retards age-related tissue degeneration. Therefore, interventions that improve skin metabolism and mitochondrial function provide a promising means to maintain skin health in old age.

Endurance exercise induces metabolic adaptations via activation of the transcriptional co-activator, peroxisome proliferator-activated receptor γ coactivator-1 α (PGC-1α). PGC-1α is the master regulator of mitochondrial metabolism and biogenesis, and has been touted as a potential therapeutic target for aging-associated diseases, including diabetes. Interestingly, mild over-expression of PGC-1α in skeletal muscle alone is known to be protective against sarcopenia, to attenuate inactivity-induced fiber atrophy, to ameliorate ALS pathology, to reduce systemic chronic inflammation, and to maintain systemic glucose and insulin homeostasis in aged mice.

Accordingly, it would be desirable to further understand the metabolic effects of exercise in order to develop novel therapies capable of inducing mitochondrial biogenesis and improving skin and muscle health.

SUMMARY OF THE INVENTION

It has now been determined that the protein, interleukin-15 (IL-15), induces mitochondrial biogenesis, and thus, is therapeutically useful in the treatment of pathologies associated with reduced mitochondrial metabolism or mitochondrial dysfunction.

Thus, in one aspect of the invention, a method of inducing mitochondrial biogenesis in a mammal is provided comprising the administration of interleukin-15 or nucleic acid encoding interleukin-15 to the mammal.

In another aspect of the invention, a method of treating skin and muscle pathologies is provided. The method comprises administration of interleukin-15 or nucleic acid encoding interleukin-15 to a mammal in need of such treatment.

In another aspect of the invention, a composition useful to induce mitochondrial biogenesis is provided comprising interleukin-15 or nucleic acid encoding interleukin-15 in combination with a pharmaceutically acceptable carrier.

These and other aspects of the invention will be described by reference to the following figures.

Figure 4:
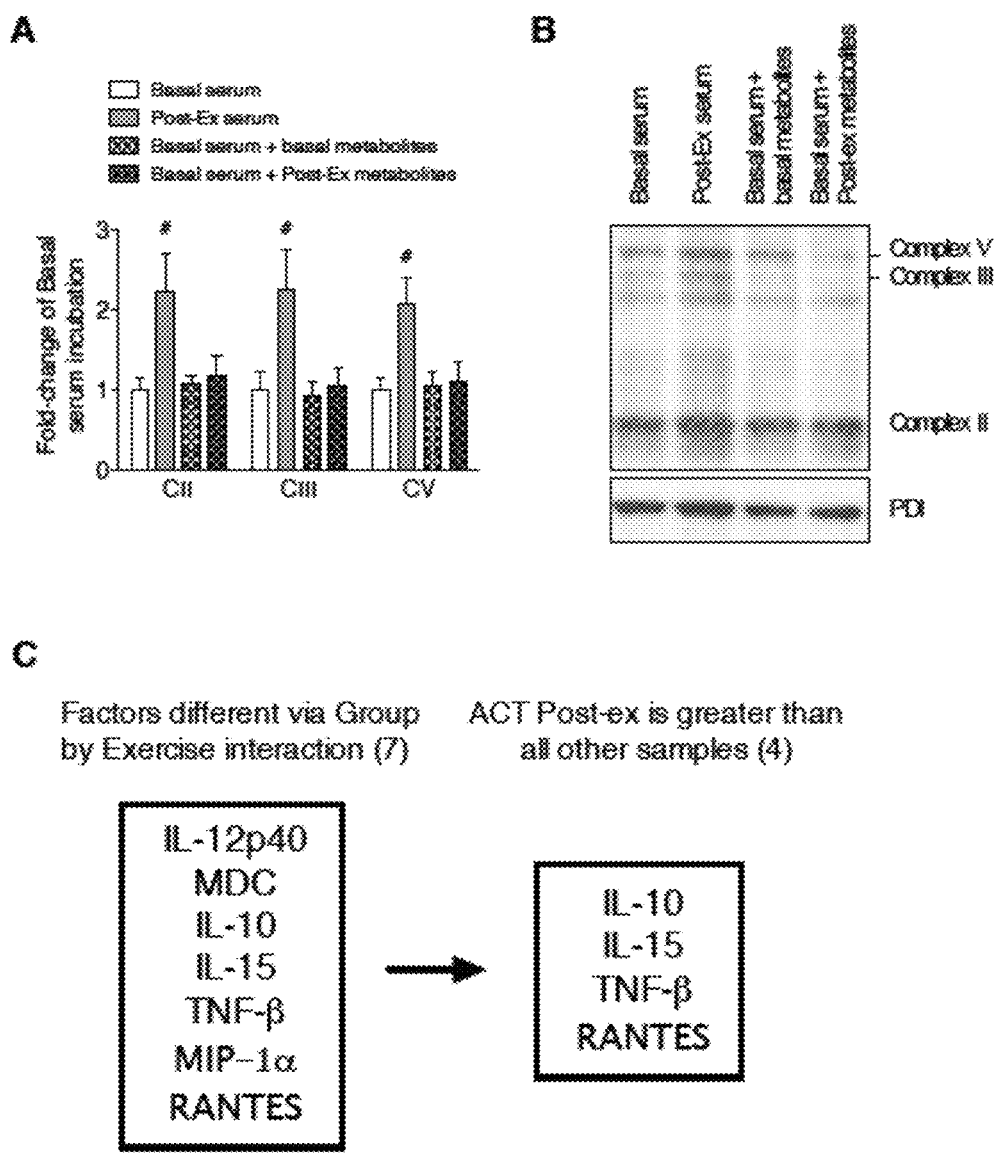
Figure 5:
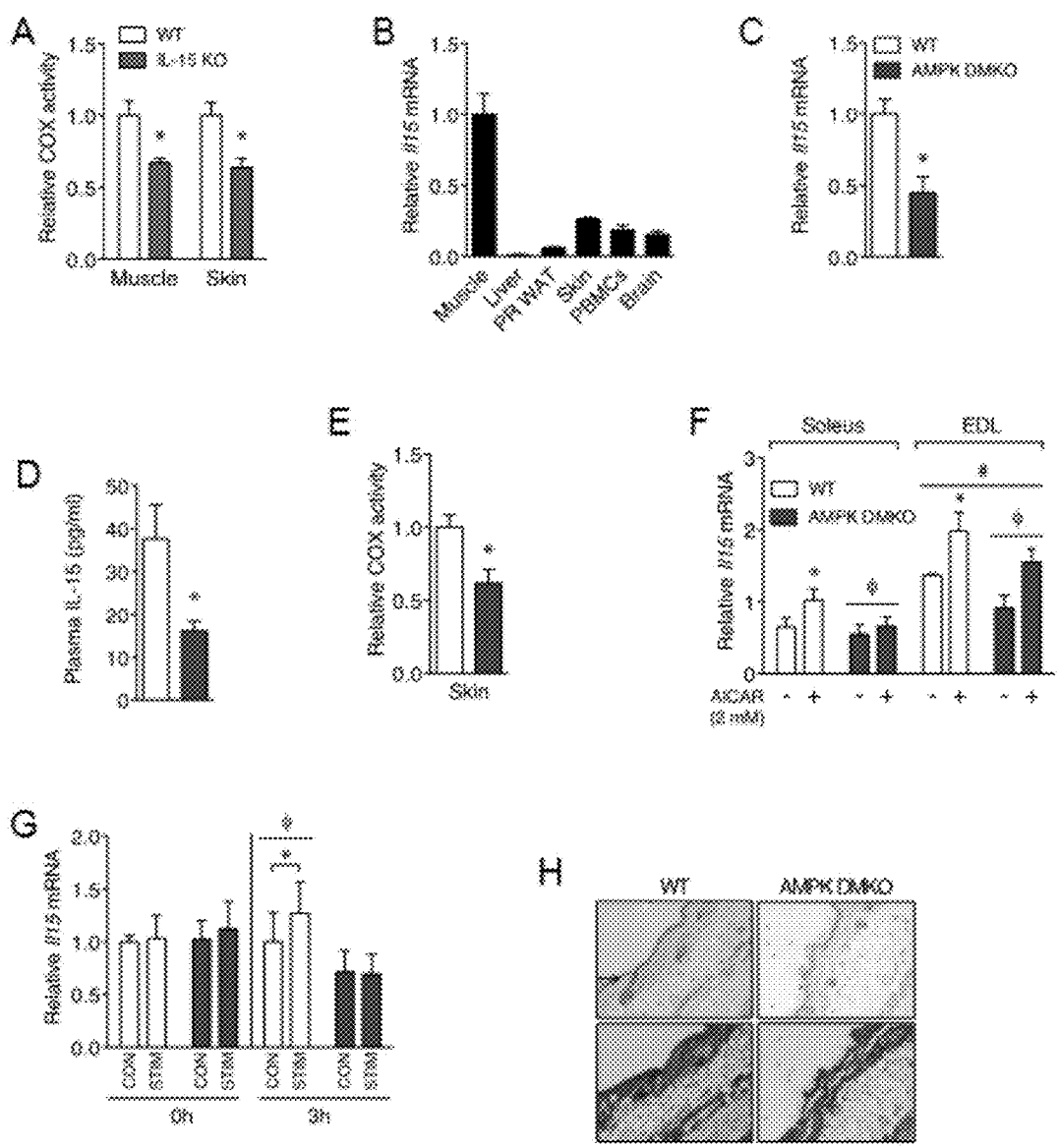

Expression of Pgc-1α mRNA in buccal swabs before and after exercise; (B) Immunoblots of mitochondrial protein subunits of complex III (core 2) and complex IV (COX II) in primary dermal fibroblasts; (C) Criteria used to analyze the results of a plasma cytokine panel for determination of factors induced by exercise that are likely to signal peripheral tissue mitochondrial biogenesis; (D) The percent change in plasma TNF-β, IL-15 and IL-10 in SED and ACT groups in response to a single bout of exercise; (E) Immunoblots of mitochondrial complex III protein in primary dermal fibroblasts incubated for 48 hours in enriched media containing 10% basal or post-exercise (post-ex) serum from ACT subjects that was pre-treated with control IgG, anti-TNF-β, anti-IL-15, or IL-10 neutralizing antibodies (n=4 replicates per condition); (F) Oxygen consumption rate (OCR) and; (G) cell counts of human primary dermal fibroblasts treated with the indicated concentrations of rhIL-15 for 48 hours (n=3); (H) qPCR of Pgc-1α mRNA in tissues from wild-type mice that were sacrificed at the indicated times after cessation of exercise or that did not exercise (SED) (Muscle is quadriceps tissue, n=9 per group); (I) Corresponding serum IL-15 concentration at the indicated times post-exercise (n=9 per group); (J) Pgc-1α mRNA expression in quadriceps muscle and skin; and (K) Cytb mRNA in skin harvested from wild-type mice that rested (SED) or were subjected to treadmill exercise in conjunction with tail vein injection of a total of 5 μg of IgG control or 2.5 μg anti-IL-15 antibody. Data in A, C, D were compared using a two-way repeated measures ANOVA. Data in F-K were compared using a one-way ANOVA. *P<0.05 from basal condition, control or SED group. #p<0.05 from EX+IgG. †P<0.05 from all other conditions. ND, not detectable. Data are mean±SE;

FIG. 4 illustrates serum deproteinization, analyte screen results and mouse PGC-family member mRNAs with IL-15 neutralization. (A) Mitochondrial protein expression in dermal fibroblasts treated with basal, post-exercise serum, basal serum with ethanol precipitated basal serum, or basal serum with ethanol precipitated post-exercise serum, (B) representative immunoblots. n=4 per treatment, (C) Factors identified by a 2-way repeated measures ANOVA to be uniquely affected in the ACT post-exercise plasma samples, (D) mRNA expression of mitochondrial regulators Pgc-1β and (E) Pprc1 in skin tissue from mice that remained sedentary or exercised in conjunction with injection if IgG control or anti-IL-15 neutralizing antibody. n=6-10 per group. #Significantly different (P<0.05) from all other treatments. *Indicates a significant (P<0.05) difference from the indicated group(s). Data are mean±SE;

FIG. 5 graphically illustrates that IL-15 expression and skin metabolism are regulated by skeletal muscle AMPK. (A) Cytochrome c oxidase (COX) activity relative to WT mice in skeletal muscle (quadriceps), and skin tissue from WT and IL-15 KO mice, (B) Relative Il15 mRNA expression in body tissues, (C) Il15 mRNA in gastrocnemius muscle and (D) plasma IL-15 levels in 3 month old wild-type littermates (WT) and AMPK β1β2 double muscle knock-out (AMPK DMKO) mice, (E) Cytochrome c oxidase activity in skin from WT and AMPK DMKO mice, (F) Il15 mRNA expression in isolated EDL and soleus muscles from WT and AMPK DMKO mice that were incubated with 2 mM AICAR or vehicle for 2 hours, (G) Il15 mRNA expression in tibialis anterior muscle from WT and AMPK DMKO mice that were subjected to STIM, (H) Histological images of skin from 18-month-old wild-type and AMPK DMKO littermates stained with H&E or trichrome (black arrowhead is the stratum spinosum and the white asterisk indicates the dermis), (I) Quantification of skin dermal collagen and (J) stratum spinosum thickness in aged WT and AMPK DMKO mice. n=5. mRNA expression was normalized to Gapdh or β-actin as a stable housekeeping gene. Results in A, C-E and I-J were compared using an unpaired t-test. Data in F were analyzed using a 3-way ANOVA. G was compared using 2-way repeated measures ANOVA. *Significantly different (P<0.05) from the indicated group. φ Main effect of genotype. #Main effect of treatment. Data are mean±SE.

Figure 6:
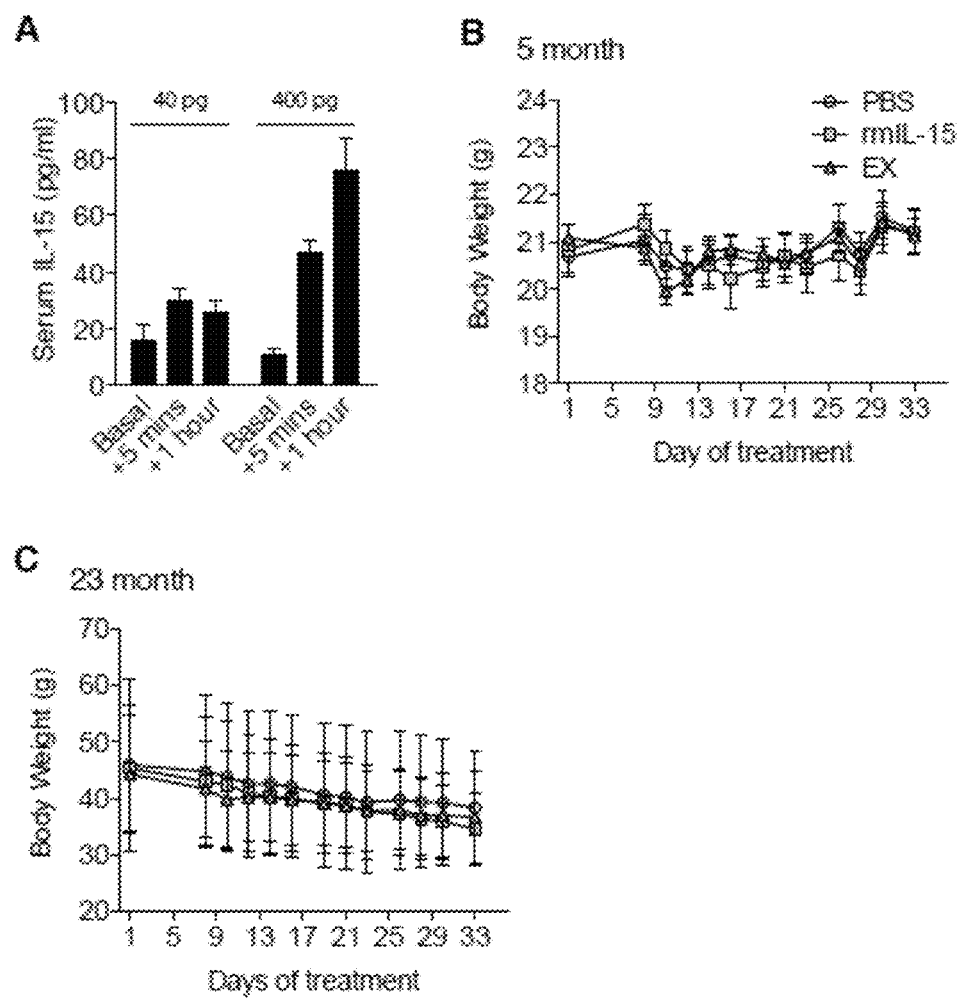
Figure 7:
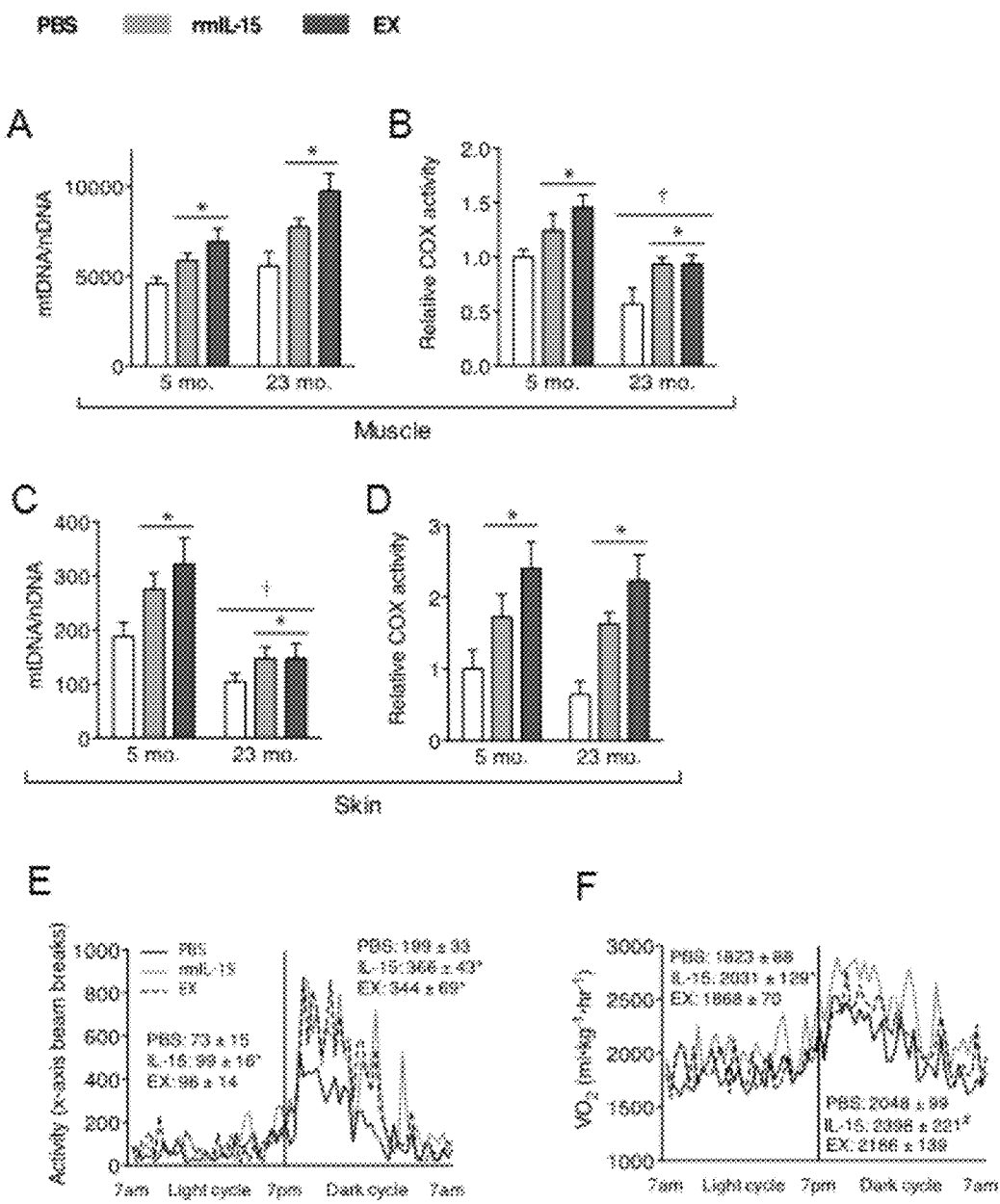
Figure 8:
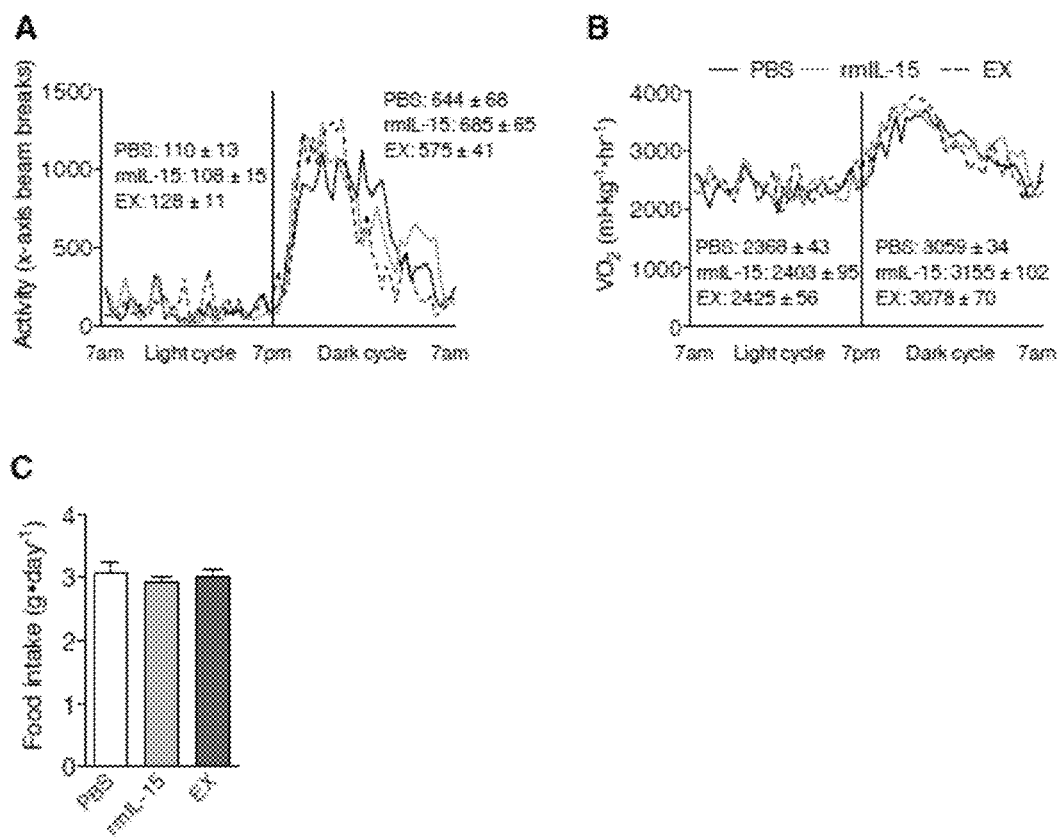
Figure 9:
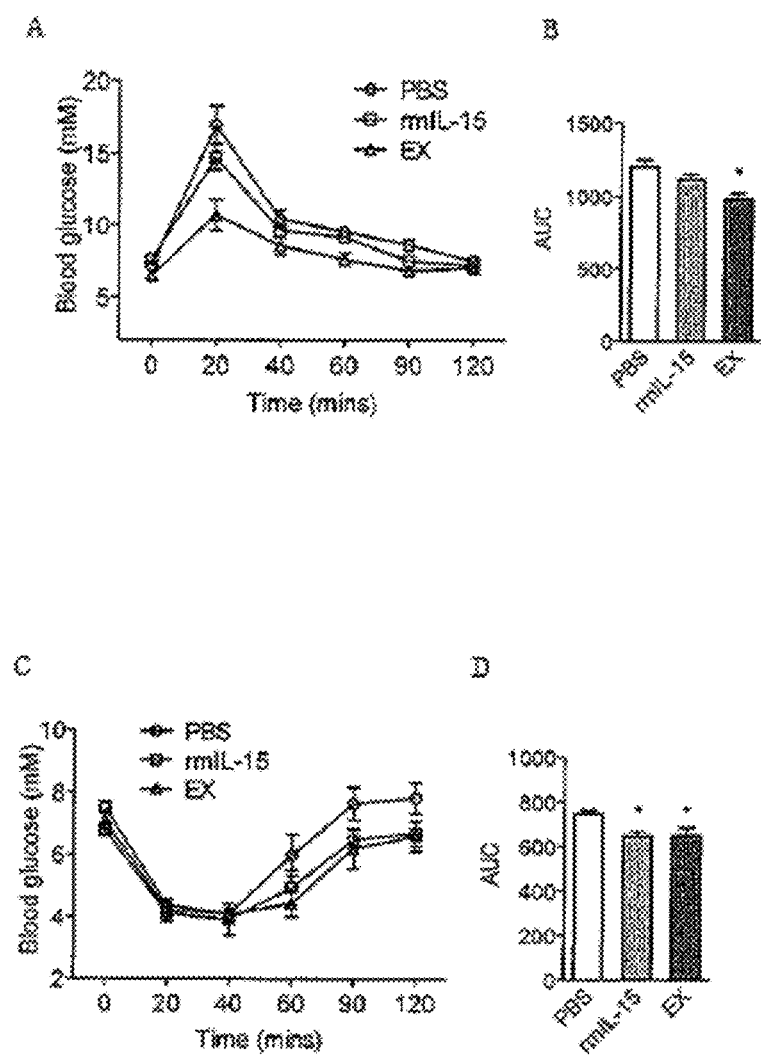
Figure 12:
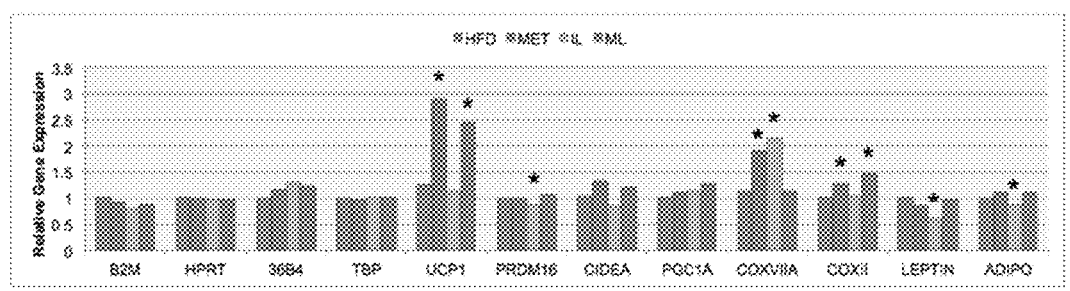
Figure 12:
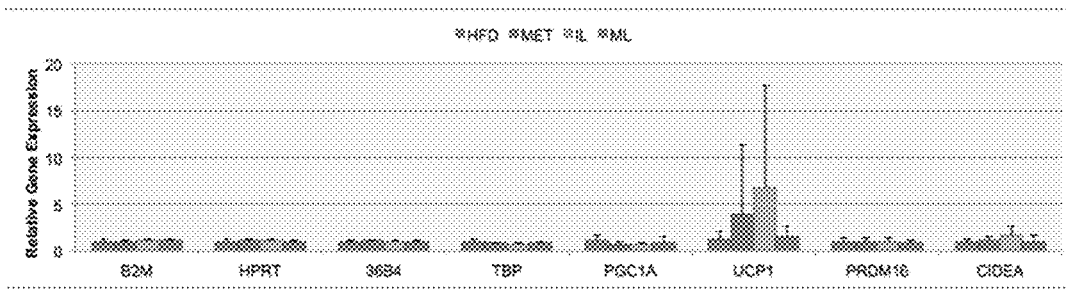

FIG. 6 graphically illustrates the effects of recombinant IL-15. (A) Serum IL-15 levels in mice injected with 40 or 400 pg of rmIL-15 at the indicated time-points relative to injection, (B) Body weights of 5 month and (C) 23 month old mice during the injection treatment period, (D) Tissue weights in 5 month and (E) 23 month old mice collected at the end of the treatment period upon sacrifice (PR WAT and gWAT are perirenal and gonadal white adipose tissue, respectively), (F) Heart weights and (G) exercise capacity in 5 and 23 month old mice at the end of the treatment period. #Indicates a main effect of treatment group. †Indicates a significant (P<0.05) effect of age. Data are mean±SE;

FIG. 7 illustrates effects of IL-15 therapy on (A) Quadriceps muscle mtDNA copy number and (B) cytochrome c oxidase (COX) activity, (C) Skin mtDNA copies and (D) COX activity, (E) Cage activity, (F) oxygen uptake ($VO_2$), (G) Peak grip strength in each treatment group normalized to body weight, (H) trichrome stained skin cross-sections from each treatment group, (I) dermal collagen content (white star indicates the dermis), (J) H&E stained cross-sections of skin from each group and (K) stratum spinosum thickness (arrow indicates the stratum spinosum layer). Scale bar is 100 μm. 5 month and 23 month old mice were injected with 500 and 1,000 pg of rmIL-15, respectively. n=4-8 per group. All data were compared using a two-way ANOVA. *Indicates a significant difference (P<0.05) from PBS group. †Indicates an overall effect of age. Data are mean±SE;

FIG. 8 graphically illustrates metabolic and behavioral characteristics of 5 month old treated mice. (A) Cage activity, (B) oxygen uptake and (C) food intake over a 24 hour period in 5 month old wild type mice subjected to daily PBS, rmIL-15 or EX treatment. Data are mean±SE;

FIG. 9 graphically illustrates the effects of IL-15 injections on insulin tolerance on (A) blood glucose during a glucose tolerance test after i.p. injection of 2 g/kg glucose and (B) area under the curve (AUC), and (C) blood glucose during an insulin tolerance test after i.p. injection of 0.7 U/kg insulin and (D) area under the curve (AUC);

FIG. 10 illustrates the amino acid sequences of human (A), mouse (B), rat (C) and dog (D) interleukin-15;

FIG. 11 illustrates human (A) and mouse (B) interleukin 15-encoding nucleic acid sequence; and FIG. 12 graphically illustrates the gene expression profiles of METRNL and IL-15 in inguinal (A) and epididymal fat (B).

DETAILED DESCRIPTION OF THE INVENTION

A method of inducing mitochondrial biogenesis in a mammal is provided comprising the administration of interleukin-15 or nucleic acid encoding interleukin-15 to the mammal. Induction of mitochondrial biogenesis is useful to treat skin and/or muscle pathologies.

The term "inducing mitochondrial biogenesis" or "induction of mitochondrial biogenesis" is used herein to refer to increased expression of genes associated with mitochondrial biogenesis including, but not limited to the following: PGC family members such as PGC-1α and PGC-1β, PPARδ, NRF-1, SIRT1, SIRT3, COX and AMPK; or to refer to an increased amount of mitochondrial DNA or protein content, a higher ratio of mitochondrial DNA to nuclear DNA, or an improvement in mitochondrial function such as an increase in mitochondrial enzyme activity or mitochondrial respiration.

The term "muscle pathologies" refers to muscle disease such as immune-mediated (inflammatory) myopathies, muscular dystrophies, metabolic myopathies, and congenital myopathies. Accordingly, examples of muscle pathologies include, but are not limited to the following: immune-mediated myopathies such as polymyositis, dermatomyositis, inclusion body myopathy; primary mitochondrial genetic disorders (for example, MELAS, MERRF, LHON, POLG1 mutations, CPEO and the like), aging-associated muscle pathologies such as muscle degeneration and mass loss (sarcopenia), congenital myopathies such as nemaline rod, central core/mini-core (RYR1), myotubular, congenital fiber type disproportion (e.g. SEPN1, RYR1, ACTA1), and muscle dystrophies such as Duchenne, Becker limb-girdle, facioscapulohumeral, myotonic type 1 and 2, oculopharyngeal, distal, and Emery-Dreifuss muscular dystrophy.

Skin pathologies include those conditions in which dermal collagen content is reduced, stratum corneum thickness is increased and/or stratum spinosum thickness is reduced, or other disorders of the skin, which may result from aging and degeneration of skin, e.g. intrinsic aging and extrinsic aging, environmental conditions, disease, infections, stress, wounds and the like. Examples include, but are not limited to, photoaging, actinic keratosis, basal cell carcinoma, squamous cell carcinoma and pre-cancerous lesions, vascular disorders such as stasis dermatitis, skin injuries such as pressure ulcers and skin tears, and autoimmune skin disorders such as bullous pemphigoid, benign mucous membrane pemphigoid, paraneoplastic pemphigoid and pemphigus vulgaris.

The term "intrinsic skin aging" is used herein to encompass aging of the skin due to internal physiological factors, which are genetically determined.

The term "extrinsic skin aging" is used herein to encompass aging of the skin due to a large variety of external factors that include, but are not limited to, exposure to sunlight, nicotine or pollution, and poor diet and sleep habits.

The term "interleukin-15" or "IL-15" is used herein to encompass mammalian interleukin-15 (e.g. the wildtype isoform), including human and non-human forms of interleukin-15, and functionally equivalent forms thereof. Interleukin-15 is a glycoprotein cytokine that activates a variety of signalling pathways including the JAK kinases by the phosphorylation of STAT3, STAT5 and STATE. IL-15 has 162 amino acids as shown in FIG. 10A, and examples of functionally equivalent forms thereof include, for example, isoforms and non-human forms as set out in FIG. 10B/C.

The term "functional equivalent variants" as they relate to interleukin-15 include naturally or non-naturally occurring variants of an endogenous interleukin-15 that retain the biological activity of interleukin-15, e.g. to induce mitochondrial biogenesis. The variant need not exhibit identical activity to endogenous interleukin-15, but will exhibit sufficient activity to render it useful to treat metabolic syndrome, e.g. at least about 25% of the biological activity of interleukin-15, and preferably at least about 50% or greater of the biological activity of interleukin-15. Such functionally equivalent variants may result naturally from alternative splicing during transcription or from genetic coding differences and may retain significant sequence homology with wild-type interleukin-15, e.g. at least about 70% sequence homology, preferably at least about 80% sequence homology, and more preferably at least about 90% or greater sequence homology. Such variants can readily be identified using established cloning techniques employing primers derived from interleukin-15. Additionally, such modifications may result from non-naturally occurring synthetic alterations made to interleukin-15 to render functionally equivalent variants which may have more desirable characteristics for use in a therapeutic sense, for example, increased activity or stability. Non-naturally occurring variants of interleukin-15 include analogues, fragments and derivatives thereof.

A functionally equivalent analogue of interleukin-15 in accordance with the present invention may incorporate one or more amino acid substitutions, additions or deletions. Amino acid additions or deletions include both terminal and internal additions or deletions to yield a functionally equivalent peptide. Examples of suitable amino acid additions or deletions include those incurred at positions within the protein that are not closely linked to activity. Amino acid substitutions within interleukin-15, particularly conservative amino acid substitutions, may also generate functionally equivalent analogues thereof. Examples of conservative substitutions include the substitution of a non-polar (hydrophobic) residue such as alanine, isoleucine, valine, leucine or methionine with another non-polar (hydrophobic) residue; the substitution of a polar (hydrophilic) residue with another such as between arginine and lysine, between glutamine and asparagine, between glutamine and glutamic acid, between asparagine and aspartic acid, and between glycine and serine; the substitution of a basic residue such as lysine, arginine or histidine with another basic residue; or the substitution of an acidic residue, such as aspartic acid or glutamic acid with another acidic residue.

A functionally equivalent fragment in accordance with the present invention comprises a portion of an interleukin-15 sequence which maintains the function of intact interleukin-15, e.g. with respect to inducing mitochondrial biogenesis. Such biologically active fragments of interleukin-15 can readily be identified using assays useful to evaluate the activity of selected interleukin-15 fragments.

A functionally equivalent derivative of interleukin-15 in accordance with the present invention is interleukin-15, or an analogue or fragment thereof, in which one or more of the amino acid residues therein is chemically derivatized. The amino acids may be derivatized at the amino or carboxy groups, or alternatively, at the side "R" groups thereof. Derivatization of amino acids within the peptide may render a peptide having more desirable characteristics such as increased stability or activity. Such derivatized molecules include for example, those molecules in which free amino groups have been derivatized to form, for example, amine hydrochlorides, p-toluene sulfonyl groups, carbobenzoxy groups, t-butyloxycarbonyl groups, chloroacetyl groups or formyl groups. Free carboxyl groups may be derivatized to form, for example, salts, methyl and ethyl esters or other types of esters or hydrazides. Free hydroxyl groups may be derivatized to form, for example, O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids, for example: 4-hydroxyproline may be substituted for proline; 5-hydroxylysine may be substituted for lysine; 3-methylhistidine may be substituted for histidine;

homoserine may be substituted for serine; and ornithine may be substituted for lysine. Terminal derivatization of the protein to protect against chemical or enzymatic degradation is also encompassed including acetylation at the N-terminus and amidation at the C-terminus of the peptide.

Interleukin-15, and functionally equivalent variants thereof, may be made using standard, well-established solid-phase peptide synthesis methods (SPPS). Two methods of solid phase peptide synthesis include the BOC and FMOC methods. Interleukin-15 and variants thereof may also be made using any one of a number of suitable techniques based on recombinant technology. It will be appreciated that such techniques are well-established by those skilled in the art, and involve the expression of interleukin-15-encoding nucleic acid in a genetically engineered host cell. DNA encoding interleukin-15 may be synthesized de novo by automated techniques well-known in the art given that the protein and nucleic acid sequences are known.

Interleukin-15-encoding nucleic acid molecules or oligonucleotides may also be used to increase plasma interleukin-15 levels. In this regard, "interleukin-15-encoding nucleic acid" is used herein to encompass mammalian interleukin-15-encoding nucleic acid, including human and non-human forms, and functionally equivalent forms thereof (e.g. that encode functionally equivalent interleukin-15, or nucleic acids which differ due to degeneracy of the genetic code). The sequence of the human interleukin-15-encoding gene is shown in FIG. 11A, and examples of functionally equivalent non-human forms include the sequence shown in FIG. 11B (mouse IL-15 nucleic acid) and other sequences which may be readily accessed, for example, at GenBank.

The term "oligonucleotide" refers to an oligomer or polymer of nucleotide or nucleoside monomers consisting of naturally occurring bases, sugars, and intersugar (backbone) linkages. The term also includes modified or substituted oligonucleotides comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide. Other oligonucleotides of the invention may contain modified phosphorous, oxygen heteroatoms in the phosphate backbone, short chain alkyl or cycloalkyl intersugar linages or short chain heteroatomic or heterocyclic intersugar linkages. For example, oligonucleotides may contain phosphorothioates, phosphotriesters, methyl phosphonates, and phophorodithioates. Oligonucleotides of the invention may also comprise nucleotide analogs such as peptide nucleic acid (PNA) in which the deoxribose (or ribose) phosphate backbone in the DNA (or RNA), is replaced with a polymide backbone similar to that found in peptides. Other oligonucleotide analogues may contain nucleotides containing polymer backbones, cyclic backbones, or acyclic backbones, e.g. morpholino backbone structures.

Such oligonucleotide molecules are readily synthesized using procedures known in the art based on the available sequence information. For example, oligonucleotides may be chemically synthesized using naturally occurring nucleotides or modified nucleotides as described above designed to increase the biological stability of the molecules or to increase the physical stability of the duplex formed with mRNA or the native gene, e.g. phosphorothioate derivatives and acridine substituted nucleotides. Selected oligonucleotides may also be produced biologically using recombinant technology in which an expression vector, e.g. plasmid, phagemid or attenuated virus, is introduced into cells in which the oligonucleotide is produced under the control of a regulatory region.

Once prepared and suitably purified, interleukin-15, interleukin-15-encoding oligonucleotides, or functionally equivalent variants thereof, may be utilized in accordance with the invention to induce mitochondrial biogenesis. In this regard, increasing the expression of interleukin-15 in a mammal, by administration of interleukin-15 or by administration of interleukin-15-encoding nucleic acid, results in interleukin-15 expression or over-expression in the mammal. While not wishing to be bound by any particular mode of action, upregulation of interleukin-15 results in upregulation of genes and/or metabolites which induce mitochondrial biogenesis.

Interleukin-15 or nucleic acid encoding IL-15 may be administered either alone or in combination with at least one pharmaceutically acceptable adjuvant, for use in treatments in accordance with embodiments of the invention. The expression "pharmaceutically acceptable" means acceptable for use in the pharmaceutical and veterinary arts, i.e. not being unacceptably toxic or otherwise unsuitable. Examples of pharmaceutically acceptable adjuvants are those used conventionally with peptide- or nucleic acid- based drugs, such as diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, antioxidants, preservatives, colouring agents and flavouring agents may also be present. Creams, lotions, ointments, emollients and sunscreen formulations may be prepared for topical application using an appropriate base such as a triglyceride base. Such creams, lotions, ointments, emollients and sunscreen formulations may also contain a surface active agent. Aerosol formulations may also be prepared in which suitable propellant adjuvants are used. Other adjuvants may also be added to the composition regardless of how it is to be administered, for example, anti-microbial agents may be added to the composition to prevent microbial growth over prolonged storage periods.

Interleukin-15-encoding oligonucleotides may be introduced into tissues or cells, e.g. such as cells removed from the wound, using techniques in the art including vectors (retroviral vectors, adenoviral vectors and DNA virus vectors) or physical techniques such as microinjection. Therapeutic oligonucleotides may be directly administered in vivo or may be used to transfect cells in vitro which are then administered in vivo. Administration of such cells may be achieved, for example, by encapsulated cell biodelivery.

To increase mitochondrial biogenesis in the treatment of skin and/or muscle pathologies, a therapeutically effective amount of an interleukin-15 or nucleic acid encoding interleukin-15 is administered to a mammal. As used herein, the term "mammal" is meant to encompass, without limitation, humans, domestic animals such as dogs, cats, horses, cattle, swine, sheep, goats and the like, as well as non-domesticated animals. The term "therapeutically effective amount" is an amount of the interleukin-15 or nucleic acid encoding interleukin-15 required to increase mitochondrial biogenesis, for example, in skin or muscle, while not exceeding an amount which may cause significant adverse effects. Dosages of interleukin-15, functionally equivalent variants thereof, or nucleic acid encoding interleukin-15, that are therapeutically effective will vary on many factors including the nature of the condition to be treated as well as the particular individual being treated.

Appropriate dosages of interleukin-15 or nucleic acid encoding interleukin-15 for use include dosages sufficient to result in plasma levels of interleukin-15 of between about 1-1000 pg/ml, and preferably 1-200 pg/ml, e.g. 1-100 pg/ml, 1-50 pg/ml, 1-20 pg/ml and 1-10 pg/ml. In one embodiment, appropriate dosages of interleukin-15 or nucleic acid encoding interleukin-15 for use include dosages sufficient to increase plasma levels of interleukin-15 to physiological levels of plasma IL-15 that are expressed post-exercise, such as 10-500% higher than endogenous baseline levels of IL-15, e.g. 50-250%, or 50-100%, above baseline IL-15 levels, i.e. to increase IL-15 plasma levels by between about 0.1-60 pg/ml, and preferably 1-50 pg/ml, e.g. 1-40 pg/ml, 1-30 pg/ml, 1-20 pg/ml or 1-10 pg/ml. Thus, dosages within the range of about 0.1 pg/kg to about 100 ng/kg interleukin-15 are appropriate, for example, 0.5 ng/kg to about 50 ng/kg, e.g. 1-50 ng/kg, 1-30 ng/kg, 1-25 ng/kg, 1-15 ng/kg or 1-10 ng/kg. In one embodiment, dosages within the range of about 0.1 pg/kg to about 50 ng/kg interleukin-15 are appropriate, for example, 1 pg/kg to about 40 ng/kg, e.g. 10-25 ng/kg, while dosages of nucleic acid encoding interleukin-15 that yield plasma levels of interleukin-15 in the range of about 1-1000 pg/ml, and preferably 1-200 pg/ml, e.g. 100 pg/ml, 1-50 pg/ml, 1-20 pg/ml and 1-10 pg/ml, or which increase plasma levels of interleukin-15 by between about 0.1-60 pg/ml, are appropriate.

The dosage may be delivered on a daily basis or less frequently, e.g. 2, 3, 4, 5 or 6 times per week to mimic the pulses of interleukin-15 expected with exercise training. In another embodiment, dosages of interleukin-15 protein or nucleic acid encoding interleukin-15 protein that mimic the results of an exercise regimen are used, e.g. a pulsatile dosage in an amount which increases plasma interleukin-15 levels by at least about 10% of resting endogenous levels, e.g. a dosage increasing plasma interleukin-15 protein by about 0.1-60 pg/ml or a dosage of nucleic acid encoding interleukin-15 protein that increases plasma interleukin-15 protein by about 0.1-60 pg/ml 3-5 times per week. Preferably, the dosages of interleukin-15 are no more than about 50 ng/kg and result in plasma levels of interleukin-15 which are no more than about 100 pg/ml.

In the present treatment, interleukin-15 or nucleic acid may be administered by any route suitable to increase the plasma levels thereof. Examples of suitable administrable routes include, but are not limited to, oral, subcutaneous, intravenous, intraperitoneal, intranasal, enteral, topical, sublingual, intramuscular, intra-arterial, intramedullary, intrathecal, inhalation, ocular, transdermal, vaginal or rectal means. Depending on the route of administration, the protein or nucleic acid may be coated or encased in a protective material to prevent undesirable degradation thereof by enzymes, acids or by other conditions that may affect the therapeutic activity thereof.

In one embodiment, IL-15 is used to treat pathologies of the skin, including aging skin. In this regard, IL-15 may be administered in conjunction with, e.g. at different times, in combination with, or simultaneously with, at least one other compound effective to treat pathologies of the skin. For example, IL-15 may be used in conjunction, combination or simultaneously with treatments such as corticosteroid cream or ointment, systemic corticosteroids, DMSO, coenzyme Q10, alpha lipoic acid, vitamin C, vitamin E, immune modulators or immunosuppressors, antibiotics, antihistamines, treatments that improve barrier function of the skin (sunscreens), emollients, phototherapy and the like.

In another embodiment, interleukin-15 may be administered in conjunction with one or more compounds or treatments effective to treat muscle pathologies. For example, IL-15 may be used in conjunction with treatments such as predisone, prednisolone, anabolic steroids, selective androgen receptor agonists and creatine monohydrate, myostatin inhibitors, exercise (endurance, resistance or sprint-interval) and the like.

In another embodiment, interleukin-15 may be administered in conjunction with, e.g. in combination with, simultaneously to or at different times, at least one other compound or treatment also effective to increase mitochondrial biogenesis, including but not limited to, meteorin-like protein (METRNL, for example, as depicted by GenBank Reference: NC_000017.11, including functional variants and METRNL from other species), AMPK activators (e.g. AICAR, metformin, A769662, salicylate or C24), coenzyme Q10, synthetic coenzyme Q10 analogues, PPAR agonists (e.g. bezafibrate, gemfibrozil), exercise (endurance, resistance or sprint-interval) and the like.

Embodiments of the invention are described in the following specific examples which are not to be construed as limiting.

EXAMPLE 1

Determination of Activity of IL-15 to Induce Mitochondrial Biogenesis

Methods and Materials

Human Subject Recruitment and Testing

Human subjects for sedentary (SED) and active (ACT) groups were recruited as previously described (Crane et al. *J Gerontol A Biol Sci Med Sci* 68, 631-8 (2013), the contents of which are incorporated herein by reference). Tissue samples from human subjects were collected following an overnight fast. Skin samples were acquired from the upper portion of the non-sun exposed buttocks below the waistline using a 4 mm punch biopsy under local anaesthetic without norepinephrine. Subcutaneous fat was separated from the bottom portion of the dermis following tissue collection. Buccal swabs, and plasma and serum samples were collected at rest and following acute exercise. All samples were flash frozen in liquid nitrogen. After baseline tissue collections, subjects underwent a bout of exercise testing to confirm aerobic fitness, as described by Crane et al. 2013, ibid. Within 5 minutes of finishing, each subject then underwent 30 minutes of exercise at 50% of their cycling power maximum. In total the subjects cycled for approximately 45 minutes each. A buccal swab was collected immediately at the end of this exercise session.

Sample Analysis

Plasma (EDTA) cytokines from human subjects were initially analyzed using a 42-analyte multiplex ELISA assay (Millipore) and subsequent mouse IL-15 analyses were performed as a single-plex ELISA. GM-CSF, IFN-γ, IL-10, IL-12 (p70), IL-13, IL-1β, IL-2, IL-4, IL-5, IL-6, IL-7, IL-8 and TNF-α were assessed using high sensitivity ELISAs (0.13-2,000 pg/ml) and all other analytes were analyzed using standard detection limits (3.2-10,000 pg/ml). Proteins in human serum were precipitated using ethanol, followed by centrifugal pelleting of the precipitant and removal of the supernatant that contained soluble metabolites. The supernatant fraction was then dried using a vacuum centrifuge and the metabolites were resuspended in sterile water to the original serum volume. The removal of all proteins was confirmed using a protein assay and this fraction was added to intact serum for cell culture experiments as indicated. Primary human dermal fibroblasts were cultured according to standard explant methods.

Cell and tissue lysates were prepared using 0.05 M potassium phosphate buffer and mitochondrial protein immunoblotting was performed as described using human or rodent antibodies from Abcam (#ab110411, #ab110413). Cytochrome c oxidase activity was performed by incubating sample lysates with reduced cytochrome c and measuring the change in absorbance at 550 nm over 90 seconds in a 96-well plate. DNA and RNA isolation and qPCR of tissues was performed as described (Crane et al. *PLoS One* 8, e81879 (2013), the contents of which are incorporated herein by reference).

All mouse experiments were performed using female mice on a chow diet. IL-15 knockout mice (IL-15 KO) and C57/B16 control mice were obtained from Taconic and sacrificed at 12 weeks of age. Wild-type mice for acute exercise experiments were obtained from Jackson labs and sacrificed at 16 weeks of age. AMPK DMKO (mice lacking β1 and β2 subunits of AMP-activated protein kinase) mice and wild-type littermates were bred and housed in the McMaster University Animal Facility under standard housing conditions with a 12 h light/dark cycle. Acute exercise experiments were performed at a speed of 16 meters per minute at an uphill grade of 10 degrees. All neutralizing antibodies were purchased from R&D Systems.

Ex Vivo and in Situ Muscle Experiments.

Soleus and EDL muscles were excised under anaesthesia from AMPK DMKO mice and wild-type littermates and incubated in 1 ml of media at 30° C. for 2 hours with and without AICAR (5-aminoimidazole-4-carboxamide-1-β-D-ribofuranoside) before being removed and snap frozen. In situ contraction experiments were performed by first isolating the tibialis anterior (TA) muscle under anaesthesia (Ketamine/Xylazine) from both legs and connecting the distal tendon of one leg to a force transducer with string. The sciatic nerve of that leg was then exposed and enervated using pulsed electrical stimulation 400 times at 1.5-4 milliamps at a frequency of 10 Hz for 0.5 seconds over the course of 30 minutes and the contralateral leg served as a non-stimulated control. Mice were maintained on a 33° C. peltier warmed block under isofluorane gas anaesthetic during the contraction and recovery periods using a carrier gas of 95% oxygen. TA muscles were harvested immediately following (0 h) the contraction protocol or after 3 hours.

Grip strength was tested in mice as described (Ogborn et al., *Can J Neural Sci* 39, 225-31 (2012), the relevant contents of which are hereby incorporated by reference). Mouse behavior (cage activity, food intake) and metabolic parameters (VO2, VCO2, RER) were analyzed using Columbus Live Animal Monitoring System (CLAMS, Columbus instruments) over a 24-hour period with lights on at 0700 and off at 1900 hours.

C57/BL6 mice that were 5 and 23 months old were randomly allocated to vehicle (PBS), recombinant IL-15 (rmIL-15) or exercise daily treatment for 33 consecutive days. rmIL-15 (5 month group: 500 pg; 23 month group: 1,000 pg) or vehicle control (PBS) was injected via the tail vein using a tuberculin syringe. This dosing was used based on pilot work in 3-4 month old mice (FIG. 6A) and because the 23 month old mice weighed approximately twice as much as the 5 month old mice at the start of the experiment.

Exercise trained mice underwent 33 consecutive days of forced treadmill running. The first week of exercise training occurred at a treadmill speed of 16 meters per minute for 5 month old mice and 10 meters per minute for 23 month old mice at a 10-degree uphill grade for 1 hour. After one week, the 23 month old group was increased to 12 meters per minute and after 2 weeks increased to 14 meters per minute. After the first week, 5 month old mice were increased to 18 meters per minute for the remainder of the training period. Grade and duration remained unchanged for the training period.

Results

Figure 1:
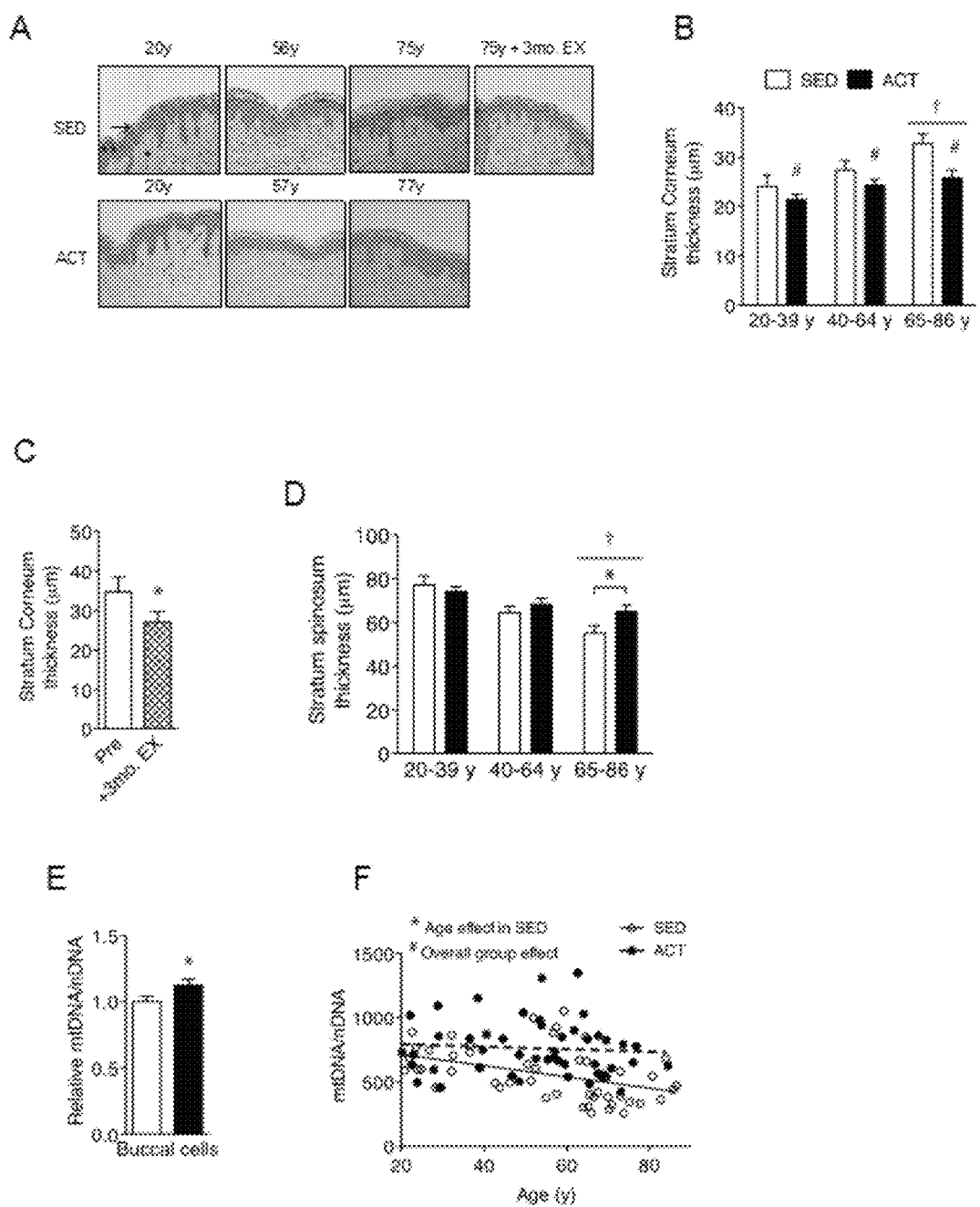
FIG. 1 illustrates that exercise reverses aspects of aging in human skin and increases mitochondria as shown by (A) representative images of skin cross sections from active (ACT) and sedentary (SED) individuals (black arrow indicates the stratum corneum layer, double asterisk indicates the stratum spinosum and single asterisk indicates the dermis); (B) Stratum corneum thickness in SED and ACT subjects across the lifespan, (C) Stratum corneum thickness before and after 3 months of aerobic exercise training in previously sedentary elderly (65-86y) adults, (D) Stratum spinosum layer thickness in SED and ACT subjects in various age groups, (E) mtDNA copy number in buccal cells and (F) skin samples from habitually sedentary (SED) and highly active (ACT) individuals, (G) mtDNA copy number in SED 65-86 year old skin samples before and after 3 months of aerobic exercise training, (H) mRNA expression of Cox7b in basal buccal cell samples from 20-86 year old SED and ACT subjects. n=11-19 per age and activity group. Cross sectional analyses and comparisons were made using a two-way ANOVA. n=10 for subjects that underwent the 3-month aerobic exercise intervention. Pre/post training comparisons were made using a paired t-test. *Indicates a significant (P<0.05) difference from the indicated group(s). #Indicates a significant (P<0.05) overall activity group effect. †Indicates a difference (P<0.05) from 20-39 y individuals.
Figure 2:
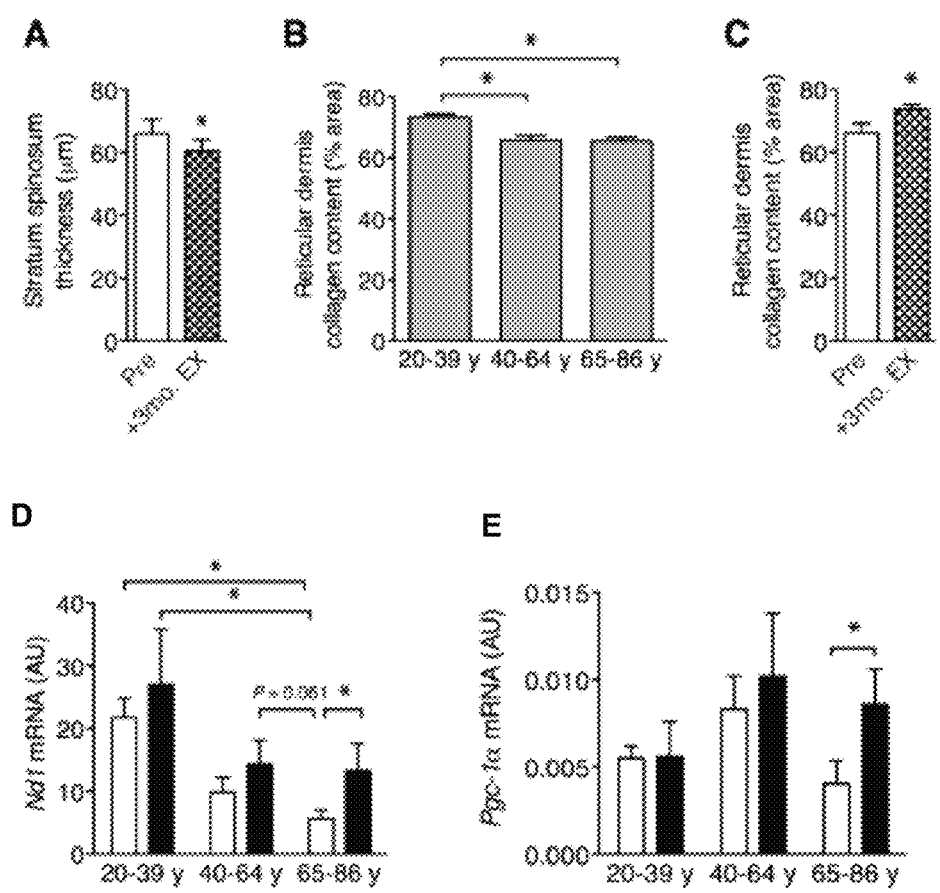
FIG. 2 graphically illustrates human skin structure quantification and buccal cell mitochondrial gene expression, including; (A) Stratum spinosum thickness in skin samples from SED 65-86 year old subjects before and after 3 months of endurance exercise training, (B) Reticular dermis collagen content in skin from each age group, (C) Reticular dermis collagen content in skin in SED 65-86 year old subject before and after 3 months of endurance exercise, (D) Buccal cell mRNA expression of the mitochondrial genes Ndl and (E) Pgc-1α in SED and ACT adult subjects. n=11-19 per age and activity group. Cross sectional analyses and comparisons were made using a two-way ANOVA. n=10 for subjects that underwent the 3-month aerobic exercise intervention. Pre and post-3 month exercise training comparisons were made using a paired t-test. *Indicates a significant (P<0.05) difference from the indicated group(s). Data are mean±SE.

It was found that the typical age-related thickening of the stratum corneum epidermal layer was reduced in highly aerobically active subjects (ACT, ≥4 hours/week of high-intensity exercise) compared to sedentary controls (SED, ≤30 minutes/week of exercise, FIG. 1A-B). Moreover, in sedentary elderly adults (SED>65 years old), 3 months of endurance exercise training reduced stratum corneum thickness (FIG. 1C). The oldest (65-86 y) ACT subjects also had attenuated thinning of the stratum spinosum layer of the epidermis compared to the SED subjects (FIG. 1D), and unexpectedly, 3 months of exercise training reduced stratum spinosum thickness (FIG. 2A). Habitual exercise had no influence on the age-related loss of reticular dermis collagen (FIG. 2B); however, endurance exercise training in elderly SED subjects did increase collagen content (FIG. 2C-D). mtDNA content and gene expression in ACT and SED subjects in skin and buccal cell (cheek swab) tissue samples was also assessed. It was found that mtDNA copy number in buccal cells and skin was greater in ACT versus SED subjects (FIG. 1E-F) and that, in parallel to the changes in skin structure, 3 months of aerobic exercise increased skin mtDNA copy number in sedentary older adults (FIG. 1G). In support of these mtDNA changes, basal levels of buccal cell mitochondrial genes were only maintained with age in ACT subjects (Cox7b, FIG. 1H; Nd1 and Pgc-1α, FIG. 2D-E). These findings indicate that exercise can attenuate aspects of skin aging in humans and that these changes are associated with improvements in tissue mitochondria.

Figure 3:
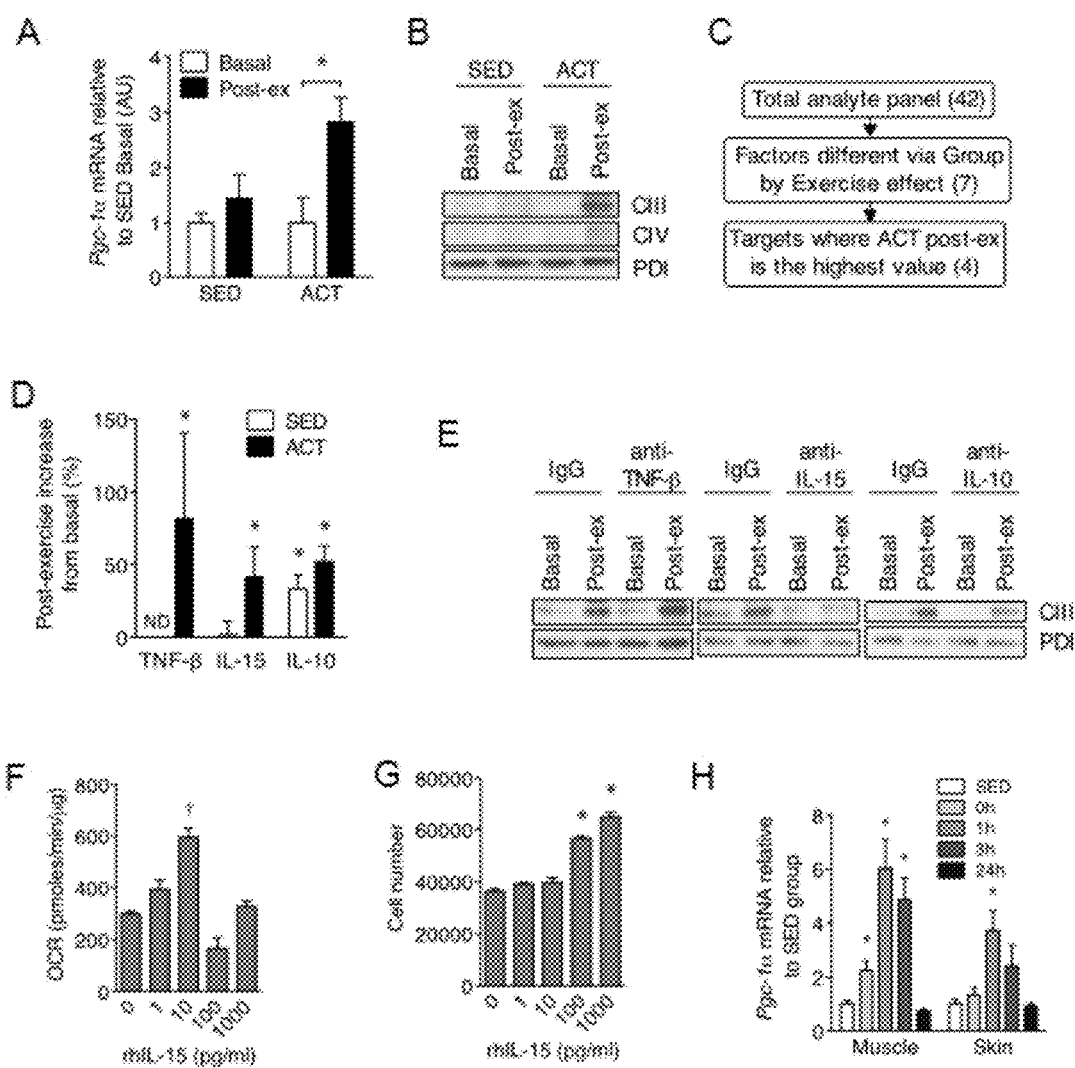
FIG. 3 graphically illustrates that L-15 is responsible for exercise-stimulated mitochondrial biogenesis in epithelium (skin and cheek cells) in vitro and in vivo as shown by: (A)

It was then determined whether or not ACT individuals produced a unique response to acute exercise that might explain the differences in skin tissue mitochondria. When young subjects from each activity group undertook a single session of cycling exercise, only the ACT group induced a significant increase in Pgc-1α mRNA expression in buccal cells acquired immediately afterwards (FIG. 3A). To determine if a circulating factor was mediating the mitochondrial effect, human primary dermal fibroblasts were incubated in media conditioned with 10% human serum acquired from young SED and ACT individuals prior to and following acute exercise. ACT post-exercise serum conditioned media increased mitochondrial content in fibroblasts (FIG. 3B). To confirm that a protein was responsible for the exercise effect, all serum proteins were removed using ethanol precipitation, which completely ablated the mitochondrial effect of the ACT post-exercise sera (FIG. 4A-B). Plasma samples from these subjects were then evaluated before and after exercise using a panel of known cytokines and chemokines in order to screen for proteins that were uniquely altered in the ACT post-exercise condition (FIG. 3C). This analysis produced four candidate proteins: TNF-β, IL-15 and IL-10 and RANTES (FIG. 4C). Since RANTES has only been associated with inflammation, the remaining analytes were tested to determine which was essential to the mitochondrial response by pre-treating the serum with neutralizing antibodies to TNF-β, IL-10 or IL-15. It was found that only anti-IL-15 antibodies mitigated the increase in mitochondrial protein in the fibroblasts (FIG. 3E). It was then determined whether or not IL-15 stimulates mitochondrial function in a dose dependent manner by measuring oxygen consumption in dermal fibroblasts treated with a range of recombinant human IL-15 (rhIL-15) between 0 and 1,000 pg/ml. Mitochondrial function improved with rhIL-15 doses of 1 and 10 pg/ml (FIG. 3F). To the contrary, rhIL-15 doses of 100 pg/ml and 1,000 pg/ml decreased mitochondrial function in human dermal fibroblasts, indicating a narrow window of therapeutic effectiveness that corresponds closely to the levels of IL-15 that are endogenously expressed in human plasma following exercise (5.6±1.2 pg/ml). Similarly, the rhIL-15 doses of 100 pg/ml and 1,000 pg/ml caused an increase in dermal fibroblast proliferation versus control, indicative of the undesirable progression towards cancerous cell growth (FIG. 3G) This narrow dosage range established suggests that for therapeutic use, it would be advantageous to administer IL-15 in a dose that would mimic the physiological levels of plasma IL-15 that are expressed post-exercise, such as 10-500% higher than baseline IL-15, e.g. 50% above baseline IL-15 levels.

Since exercise improves skeletal muscle mitochondrial capacity in part through the up-regulation of Pgc-1α, it was determined whether or not this occurred acutely in skin. It was found that a single session of treadmill running in mice caused a transient elevation in Pgc-1α mRNA in both skeletal muscle and skin, peaking at 1 hour post-exercise (FIG. 3H), paralleling the rise in serum IL-15 (FIG. 3I). In order to determine whether IL-15 was necessary for exercise-stimulated mitochondrial biogenesis in vivo, wild-type mice were given a venous injection of IL-15 neutralizing antibody or IgG control prior to and following 1 hour of treadmill exercise. It was found that neutralizing circulating IL-15 antibody partially reduced the exercise-induced elevation in skeletal muscle Pgc-1α expression, but not skin Pgc-1α expression (FIG. 3J). Pgc-1β expression was not affected by the IL-15 neutralizing antibody (FIG. 4D). However, IL-15 neutralizing antibodies prevented an exercise-stimulated reduction in skin PPARγ coactivator-related protein 1 (Pprc1) mRNA (FIG. 4E) and importantly abolished an increase in downstream mitochondrial gene expression of cytochrome b (FIG. 3K). These results indicate that IL-15 mediates a portion of exercise stimulated mitochondrial biogenesis in skin and skeletal muscle, although this regulation appears to be controlled via tissue specific mechanisms.

It was then determined whether or not IL-15 was necessary for the basal maintenance of mitochondrial function. Tissue mitochondria in mice lacking whole-body expression of IL-15 (IL-15 KO) were then evaluated and lower cytochrome c oxidase (COX) enzyme activity in skin and skeletal muscle tissue from IL-15 KO mice (FIG. 5A) was found. IL-15 is a well-described cytokine expressed in many cell types whose expression is high in skeletal muscle and secondarily in skin when compared across metabolic tissues (FIG. 5B). Since acute exercise capacity was predictive of the positive effects on skin tissue in human subjects (20-39 y VO$_2$ peak, SED: 34±2 ml/kg/min, ACT: 57±2 ml/kg/min), this implicated the involvement of muscle AMP-activated protein kinase (AMPK), a well-described energy-sensing molecule that regulates exercise capacity. It was tested whether or not AMPK was involved in the expression and/or induction of IL-15 via exercise by using mice that lacked both the β1 and β2 subunits of AMPK in skeletal muscle (AMPK DMKO). These mice exhibit exercise intolerance due to reduced muscle mitochondrial content and contraction-stimulated glucose uptake but appear phenotypically normal at rest compared to wild-type littermates. Muscle IL-15 mRNA expression and plasma IL-15 were found to be reduced in AMPK DMKO mice (FIG. 5C to D) and, similar to the Il15 KO mice, AMPK DMKO mice had reduced COX activity in skin tissue (FIG. 5E). To further explore whether muscle AMPK was necessary for the stimulation of Il15 expression, skeletal muscle from WT and AMPK DMKO mice ex vivo was incubated in the presence or absence of the AMPK activator, AICAR. AICAR produced an increase in Il15 in both soleus and EDL muscles in wild-type, but not AMPK DMKO mice (FIG. 5F). To more closely mimic the exercise response, contraction-mediated Il15 expression was examined by subjecting tibialis anterior (TA) muscles to a 30-minute contraction protocol, matching the work performed by WT and DMKO mice (average force per contraction over 400 contractions—WT: 236±11 mN, AMPK DMKO: 232±10 mN). The stimulated (STIM) and contralateral resting muscle (CON) were harvested immediately (0 h) or 3 h following the cessation of contractions. No changes in Il15 mRNA were present at the 0 h time point, but Il15 expression was specifically increased in wild-type but not AMPK DMKO 3 h after the muscle contractions (FIG. 5G), indicating that contraction-stimulated Il15 expression is dependent on AMPK activity. Furthermore, skin morphology in aged (18 month old) WT and AMPK DMKO mice was analyzed and reduced collagen content (FIG. 5H-I) and reduced dermal thickness in AMPK DMKO mice was found (FIG. 5J), consistent with a phenotype of accelerated skin aging. Overall, these results indicate that IL-15 is regulated by muscle AMPK and that skeletal muscle can regulate skin morphology.

Since IL-15 appears to regulate exercise-stimulated mitochondrial signaling in skin and skeletal muscle, it's therapeutic potential in young (5 month) and old (23 month) mice was determined with daily intravenous injections of recombinant mouse IL-15 (rmIL-15) that mimicked the physiologic elevation of endogenous IL-15 observed following acute exercise (FIG. 6A). Both young and old mice that received rmIL-15 injections or were treadmill-exercised had significantly higher skin and muscle COX activity, and mtDNA copy number (FIG. 7A-D). However, there was no change in body or tissue mass in any of the groups (FIG. 6B-F) and only the exercise group had an increase in treadmill running capacity (FIG. 6G). Moreover, oxygen consumption, cage movement and food intake were similar amongst 5 month old mice (FIG. 8A-C), indicating that behavioural changes did not account for the changes in mitochondria. However, both rmIL-15 and exercise treatment resulted in higher cage activity and oxygen consumption in 23 month old mice (FIG. 7E-F), indicating a partial restoration of mobility and hence, muscular functionality specifically in the aged mice. As seen in the 5 month groups, 23 month old mice had similar food consumption (FIG. 8C). Despite no change in muscle mass, rmIL-15 and exercise treatment also increased muscle grip strength in 5 month old mice, indicating improved muscle function (FIG. 7G). Additionally, rmIL-15 and exercise treatment resulted in higher stratum spinosum thickness and dermal collagen content in 23 month old mice compared to PBS treated mice, which partially reversed the effects of skin aging (FIG. 7H-J).

EXAMPLE 2

Effect of IL-15 on Glucose and Insulin Tolerance

Studies in the mice were also conducted to determine oral glucose tolerance, and exercise (gold standard to induce insulin sensitivity) was shown to significantly improve glucose tolerance. Mice were injected once daily via tail vein with PBS, 500 pg of recombinant mouse IL-15 (rmIL-15) or underwent forced exercise (EX) training for 33 consecutive days.

IL-15 was shown to improve aspects of glucose metabolism/regulation (FIG. 9A-B). The IL-15 injected mice exhibited oral glucose tolerance results that were intermediate between the control (PBS) and exercised mice (FIG. 9B/C). An insulin tolerance test was conducted in which insulin was injected into mice. Mice sensitive to insulin show a greater drop in glucose. This data shows that the IL-15 and exercised mice show similar and improved (vs saline injected control animals) insulin sensitivity (i.e. less risk for diabetes) (FIG. 9C/D).

EXAMPLE 3

Effect of IL-15 Combined with METRNL

In this experiment, the combined effect of IL-15 with another compound effective to increase mitochondrial biogenesis was determined. In this case, the compound selected was METRNL.

Recombinant IL-15 (25 ng/kg) and METRNL (0.4 ng/kg) were given intravenously to high-fat fed (HFD) C57BL/6 mice, 3 days a week for six weeks.

As shown by the relative mRNA gene expression profiles from samples taken from the treated mice (see FIG. 12), METRNL rescues diet-induced obesity and diabetes by mediating muscle mitochondrial adaptations and browning of the fat (upregulates UCP1 more strongly than IL-15 in inguinal fat), while IL-15 exerts a stronger effect on mitochondrial signaling in skin (as shown by UCP1 upregulation in epididymal fat).

Thus, IL-15 may be combined with other compounds to provide a complimentary effect, e.g. an increase in mitochondrial biogenesis and/or signaling in different tissue types.

The invention claimed is:

1. A method of inducing mitochondrial biogenesis in a mammal comprising the step of administering mammalian interleukin-15, or a nucleic acid encoding mammalian interleukin-15 to the mammal.

2. The method of claim 1, wherein interleukin-15 is administered as a dosage in the range of about 0.1 pg/kg to 50 ng/kg, or interleukin-15-encoding nucleic acid is administered in an amount that yields a dosage of about 0.1 pg/kg to 50 ng/kg interleukin-15.

3. The method of claim 1, wherein interleukin-15 is administered in a dosage sufficient to increase plasma levels of interleukin-15 by between about 0.1-60 pg/ml, or to increase plasma levels of interleukin-15 to no more than about 100 pg/ml.

4. The method of claim 1, wherein the interleukin-15 or interleukin-15-encoding nucleic acid is administered orally, subcutaneously, intravenously, intraperitoneally, intranasally, enterally, topically, sublingually, intramuscularly, intra-arterially, intramedullarily, intrathecally, ocularly, transdermally, vaginally, rectally or by inhalation.

5. The method of claim 1, wherein the interleukin-15 or interleukin-15-encoding nucleic acid is administered in conjunction with a second therapeutic agent.

6. The method of claim 5, wherein the second therapeutic agent is an agent that induces mitochondrial biogenesis.

7. The method of claim 5, wherein the second therapeutic agent is effective to treat a skin pathology and is selected from the group of: corticosteroid cream or ointment, a systemic corticosteroid, DMSO, coenzyme Q10, alpha lipoic acid, vitamin C, vitamin E, an immune modulator or immunosuppressor, an antibiotic, an antihistamine, a sunscreen, an emollient and phototherapy.

8. The method of claim 1, for the treatment of a skin pathology.

9. The method of claim 8, wherein the skin pathology is selected from the group consisting of photoaging, actinic keratosis, carcinoma, pre-cancerous lesions, vascular disorders, skin injuries, autoimmune skin disorders, intrinsic skin aging and extrinsic skin aging.

10. The method of claim 8, wherein the interleukin-15 or nucleic acid encoding interleukin-15 is formulated for topical administration.

11. The method of claim 1, for the treatment of a muscle pathology.

12. The method of claim 11, wherein the muscle pathology is selected from the group consisting of immune-mediated myopathies, primary mitochondrial genetic disorders, aging-associated muscle pathologies and muscle dystrophies.

13. The method of claim 12, wherein the primary mitochondrial genetic disorder is selected from the group consisting of MELAS, MERRF, LHON, POLG1 mutations and CPEO, the muscle dystrophy is selected from the group consisting of Duchenne, Becker, limb-girdle, congenital, facioscapulohumeral, myotonic, oculopharyngeal, distal and Emery-Dreifuss muscular dystrophy, and immune-mediated myopathies are selected from the group consisting of polymyositis, dermatomyosistis and inclusion body myopathy.

* * * * *